(12) United States Patent
Popplewell et al.

(10) Patent No.: US 7,491,687 B2
(45) Date of Patent: Feb. 17, 2009

(54) ENCAPSULATED MATERIALS

(75) Inventors: Lewis Michael Popplewell, Morganville, NJ (US); Joseph Brain, Bussum (NL); John Gerwin Lodewijk Pluyter, Middletown, NJ (US); Yueqian Zhen, Tredyffrin, PA (US); Kaiping Daniel Lee, Morganville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 827 days.

(21) Appl. No.: 10/983,142

(22) Filed: Nov. 5, 2004

(65) Prior Publication Data

US 2005/0153135 A1 Jul. 14, 2005

Related U.S. Application Data

(63) Continuation-in-part of application No. 10/718,240, filed on Nov. 20, 2003.

(51) Int. Cl.
*C11D 3/50* (2006.01)

(52) U.S. Cl. .......................... 512/4; 426/534; 424/401; 424/70.1; 424/59

(58) Field of Classification Search ................. 424/401, 424/59, 70.1; 512/4
See application file for complete search history.

(56) References Cited

U.S. PATENT DOCUMENTS

| | | | |
|---|---|---|---|
| 2,800,457 A | 7/1957 | Green et al. |
| 3,041,288 A | 6/1962 | Anthony |
| 3,415,758 A | 12/1968 | Powell et al. |
| 3,505,432 A | 4/1970 | Neuwald |
| 3,516,846 A | 6/1970 | Matson |
| 3,516,941 A | 6/1970 | Matson |
| 3,686,025 A | 8/1972 | Morton |
| 3,798,179 A | 3/1974 | Hellyer |
| 3,861,870 A | 1/1975 | Edwards et al. |
| 3,870,542 A | 3/1975 | Ida et al. |
| 3,947,571 A | 3/1976 | Murphy et al. |
| 3,978,204 A | 8/1976 | Charle et al. |
| 4,081,384 A | 3/1978 | Pracht |
| 4,082,223 A | 4/1978 | Nozawa |
| 4,124,521 A | 11/1978 | Jedzinak |
| 4,145,184 A | 3/1979 | Brain et al. |
| 4,209,417 A | 6/1980 | Whyte |
| 4,234,627 A | 11/1980 | Schilling |
| 4,247,498 A | 1/1981 | Castro |
| 4,318,818 A | 3/1982 | Letton et al. |
| 4,387,090 A | 6/1983 | Bolich, Jr. |
| 4,395,541 A | 7/1983 | Jacquet et al. |
| 4,402,856 A | 9/1983 | Schnoring et al. |
| 4,424,134 A | 1/1984 | Sissin et al. |
| 4,428,869 A | 1/1984 | Munteanu et al. |
| 4,446,032 A | 5/1984 | Munteanu et al. |
| 4,446,042 A | 5/1984 | Leslie |
| 4,514,461 A | 4/1985 | Woo |
| 4,515,705 A | 5/1985 | Moeddel |
| 4,521,541 A | 6/1985 | Rutherford et al. |
| 4,534,891 A | 8/1985 | Boden et al. |
| 4,537,706 A | 8/1985 | Severson, Jr. |
| 4,537,707 A | 8/1985 | Severson, Jr. |
| 4,539,135 A | 9/1985 | Ramachandran et al. |
| 4,550,862 A | 11/1985 | Barker et al. |
| 4,561,998 A | 12/1985 | Wertz et al. |
| 4,597,898 A | 7/1986 | Vander Meer |
| 4,597,962 A | 7/1986 | Grollier et al. |
| 4,673,568 A | 6/1987 | Grollier et al. |
| 4,681,806 A | 7/1987 | Matkan et al. |
| 4,705,681 A | 11/1987 | Maes et al. |
| 4,714,562 A | 12/1987 | Roselle et al. |
| 4,731,243 A | 3/1988 | Lindauer et al. |
| 4,767,547 A | 8/1988 | Straathof et al. |
| 4,819,835 A | 4/1989 | Tasaki |
| 4,830,855 A | 5/1989 | Stewart |
| 4,917,920 A | 4/1990 | Ono et al. |
| 4,961,871 A | 10/1990 | Michael |
| 4,968,451 A | 11/1990 | Scheibel et al. |
| 4,973,422 A | 11/1990 | Schmidt |

(Continued)

FOREIGN PATENT DOCUMENTS

| | | |
|---|---|---|
| EP | 0 327 927 | 1/1989 |
| EP | 0 376 385 | 12/1989 |
| EP | 0 672 409 | 5/1997 |
| EP | 0 965 326 | 12/1999 |
| EP | 1 061 124 | 12/2000 |

(Continued)

OTHER PUBLICATIONS

Lochhead, et al, Encyclopedia of Polymers and Thickeners for Cosmetics, Cosmetics & Toiletries, vol. 108, May 1993, pp. 95-138.
Kashikl, On a New Type of Flocculant, Ind.Eng.Chem.Fundam., 1986, 25, pp. 120-125.
Wurzburg, et al, Modified Starches:Properties and Uses, CRC Press, Inc., Chapter 3-Cross-Linked Starches, Chapter 8-Cationic Starches and Chapter 10-Grafted Starches.

(Continued)

*Primary Examiner*—Gina C. Yu
(74) *Attorney, Agent, or Firm*—Elizabeth M. Quirk; XuFan Tseng; Joseph F. Leightner

(57) ABSTRACT

The present invention is directed to encapsulated fragrance materials. The fragrance materials are comprised of high Clog P materials or high Clog P fragrance materials along with high Clog P solvent materials. The encapsulated fragrance and solvent materials can then be further coated with a second coating, preferably a cationic coating. The selective use of solvents enables the fragrance and fragrance materials to remain in the capsules for extended periods of time without leaching from the capsule. The leaching of the flavor or fragrance materials is a problem especially in products that contain a high loading of surfactant or emulsifying materials such as laundry and oral care products.

22 Claims, 6 Drawing Sheets

U.S. PATENT DOCUMENTS

| | | |
|---|---|---|
| 5,066,419 A | 11/1991 | Walley et al. |
| 5,085,857 A | 2/1992 | Reid et al. |
| 5,112,688 A | 5/1992 | Michael |
| 5,137,646 A | 8/1992 | Schmidt et al. |
| 5,154,842 A | 10/1992 | Walley et al. |
| 5,160,655 A | 11/1992 | Donker et al. |
| 5,169,552 A | 12/1992 | Wise |
| 5,188,753 A | 2/1993 | Schmidt et al. |
| 5,194,639 A | 3/1993 | Connor et al. |
| 5,232,769 A | 8/1993 | Yamato et al. |
| 5,237,035 A | 8/1993 | O'Lenick, Jr. et al. |
| 5,275,755 A | 1/1994 | Sebag et al. |
| 5,288,417 A | 2/1994 | Bauer et al. |
| 5,288,431 A | 2/1994 | Huber et al. |
| 5,403,499 A | 4/1995 | Kiefer et al. |
| 5,411,671 A | 5/1995 | Bauer et al. |
| 5,458,809 A | 10/1995 | Fredj et al. |
| 5,458,810 A | 10/1995 | Fredj et al. |
| 5,460,752 A | 10/1995 | Fredj et al. |
| 5,466,802 A | 11/1995 | Panandiker et al. |
| 5,470,507 A | 11/1995 | Fredj et al. |
| 5,500,138 A | 3/1996 | Bacon et al. |
| 5,534,197 A | 7/1996 | Scheibel et al. |
| 5,540,853 A | 7/1996 | Trinh et al. |
| 5,545,340 A | 8/1996 | Wahl et al. |
| 5,545,350 A | 8/1996 | Baker et al. |
| 5,559,261 A | 9/1996 | Sivik |
| 5,562,849 A | 10/1996 | Wahl et al. |
| 5,565,145 A | 10/1996 | Watson et al. |
| 5,574,179 A | 11/1996 | Wahl et al. |
| 5,581,005 A | 12/1996 | Perkins |
| 5,597,936 A | 1/1997 | Perkins et al. |
| 5,618,523 A | 4/1997 | Zysman et al. |
| 5,661,118 A | 8/1997 | Cauwet et al. |
| 5,665,822 A | 9/1997 | Bitler et al. |
| 5,670,159 A | 9/1997 | Morton et al. |
| 5,674,832 A | 10/1997 | Keys |
| 5,679,630 A | 10/1997 | Baeck et al. |
| 5,703,030 A | 12/1997 | Perkins et al. |
| 5,703,034 A | 12/1997 | Offshack et al. |
| 5,705,464 A | 1/1998 | Scheper et al. |
| 5,726,144 A | 3/1998 | Dewez et al. |
| 5,731,278 A | 3/1998 | Nair et al. |
| 5,756,436 A | 5/1998 | Royce et al. |
| 5,759,990 A | 6/1998 | Wahl et al. |
| 5,776,443 A | 7/1998 | Vinski et al. |
| 5,776,883 A | 7/1998 | Vasudevan |
| 5,783,302 A | 7/1998 | Bitler et al. |
| 5,837,661 A | 11/1998 | Evans et al. |
| 5,849,313 A | 12/1998 | Fost et al. |
| 5,877,145 A | 3/1999 | Wahl et al. |
| 5,902,781 A | 5/1999 | Painter |
| 5,914,307 A | 6/1999 | DeNome et al. |
| 5,916,862 A | 6/1999 | Morelli et al. |
| 5,929,022 A | 7/1999 | Velazquez |
| 5,932,203 A | 8/1999 | Coffindaffer et al. |
| 5,935,561 A | 8/1999 | Inman et al. |
| 5,939,373 A | 8/1999 | Haeggberg et al. |
| 5,962,386 A | 10/1999 | Scheper et al. |
| 5,968,286 A | 10/1999 | Crudele et al. |
| 5,968,404 A | 10/1999 | Trinh et al. |
| 5,968,881 A | 10/1999 | Haeggberg et al. |
| 5,990,065 A | 11/1999 | Vinson et al. |
| 6,001,343 A | 12/1999 | Trinh et al. |
| 6,017,871 A | 1/2000 | Baeck et al. |
| 6,020,294 A | 2/2000 | Getty et al. |
| 6,024,943 A | 2/2000 | Ness et al. |
| 6,057,404 A | 5/2000 | Utecht et al. |
| 6,069,122 A | 5/2000 | Vinson et al. |
| 6,071,569 A | 6/2000 | Stambaugh |
| 6,106,875 A | 8/2000 | Soper et al. |
| 6,113,935 A | 9/2000 | Rodson et al. |
| 6,133,226 A | 10/2000 | Knowlton et al. |
| 6,143,707 A | 11/2000 | Trinh et al. |
| 6,146,621 A | 11/2000 | Trinh et al. |
| 6,162,423 A | 12/2000 | Sebag et al. |
| 6,180,594 B1 | 1/2001 | Fender et al. |
| 6,190,678 B1 | 2/2001 | Hasenoehrl et al. |
| 6,194,375 B1 | 2/2001 | Ness et al. |
| 6,200,554 B1 | 3/2001 | Yeoh et al. |
| 6,221,826 B1 | 4/2001 | Surutzidis et al. |
| 6,248,315 B1 | 6/2001 | Young et al. |
| 6,255,367 B1 | 7/2001 | Bitler et al. |
| 6,261,483 B1 | 7/2001 | Frank et al. |
| 6,268,431 B1 | 7/2001 | Snyder et al. |
| 6,297,203 B1 | 10/2001 | Guskey et al. |
| 6,297,210 B1 | 10/2001 | Hsu et al. |
| 6,329,057 B1 | 12/2001 | Dungworth et al. |
| 6,335,315 B1 | 1/2002 | Trinh et al. |
| 6,355,234 B1 | 3/2002 | Birtwistle et al. |
| 6,413,548 B1 | 7/2002 | Hamer et al. |
| 6,436,383 B2 | 8/2002 | Murray |
| 6,451,065 B2 | 9/2002 | Trinh et al. |
| 6,458,754 B1 | 10/2002 | Velazquez et al. |
| 6,492,462 B2 | 12/2002 | Bitler et al. |
| 6,495,058 B1 | 12/2002 | Frankenbach et al. |
| 6,509,034 B1 | 1/2003 | Calanchi et al. |
| 6,514,487 B1 | 2/2003 | Barr |
| 6,514,489 B1 | 2/2003 | Shacknai et al. |
| 6,514,504 B1 | 2/2003 | Yen et al. |
| 6,514,918 B1 | 2/2003 | Librizzi |
| 6,514,923 B1 | 2/2003 | Cheung et al. |
| 6,517,588 B2 | 2/2003 | Hopkinson |
| 6,521,589 B2 | 2/2003 | Demeyere et al. |
| 6,524,494 B2 | 2/2003 | Hart et al. |
| 6,528,046 B1 | 3/2003 | Schmenger et al. |
| 6,531,113 B1 | 3/2003 | Mougin et al. |
| 6,531,437 B1 | 3/2003 | Ryan et al. |
| 6,540,989 B2 | 4/2003 | Janchitraponvej |
| 6,544,535 B2 | 4/2003 | Sakurai et al. |
| 6,551,604 B1 | 4/2003 | Beck et al. |
| 6,555,098 B1 | 4/2003 | Murphy et al. |
| 6,569,826 B1 | 5/2003 | Chiaradonna et al. |
| 6,592,813 B1 | 7/2003 | Fox et al. |
| 6,620,777 B2 | 9/2003 | Heibel et al. |
| 6,645,479 B1 | 11/2003 | Shefer et al. |
| 2002/0016269 A1 | 2/2002 | Noda et al. |
| 2003/0005522 A1 | 1/2003 | Trinh et al. |
| 2003/0013632 A1 | 1/2003 | Santos et al. |
| 2003/0050346 A1 | 3/2003 | Hsu |
| 2003/0069164 A1 | 4/2003 | Levinson |
| 2003/0092600 A1 | 5/2003 | Shepherd, Jr. |
| 2003/0119713 A1 | 6/2003 | Heltovics et al. |
| 2003/0125222 A1 | 7/2003 | Jahns et al. |
| 2003/0158072 A1 | 8/2003 | Goodson et al. |
| 2003/0171246 A1 | 9/2003 | Boeckh et al. |
| 2003/0199412 A1 | 10/2003 | Gupta et al. |
| 2004/0071742 A1 | 4/2004 | Popplewell et al. |
| 2004/0071746 A1 | 4/2004 | Popplewell et al. |
| 2004/0072719 A1 | 4/2004 | Bennett et al. |
| 2004/0072720 A1 | 4/2004 | Brain et al. |
| 2005/0003996 A1 | 1/2005 | Santos et al. |

FOREIGN PATENT DOCUMENTS

| | | |
|---|---|---|
| EP | 0 737 183 | 9/2001 |
| GB | 1 561 389 | 2/1980 |
| WO | 95/18096 | 7/1995 |
| WO | 97/12022 | 4/1997 |
| WO | 97/12027 | 4/1997 |
| WO | WO 99/55819 | 11/1999 |
| WO | 01/05358 | 1/2001 |
| WO | WO 01/05926 A1 | 1/2001 |
| WO | 01/40430 | 6/2001 |

| | | |
|---|---|---|
| WO | 01/49817 | 7/2001 |
| WO | 01/62376 | 8/2001 |
| WO | 02/34225 | 5/2002 |
| WO | 02/34226 | 5/2002 |
| WO | 02/074430 | 9/2002 |
| WO | 02/085420 | 10/2002 |
| WO | 03/002699 | 1/2003 |

OTHER PUBLICATIONS

Barton, CRC Handbook of Polymer-Liquid Interaction Parameters and Solubility Parameters, CRC Press, Part I, Introduction.

Gmehling, et al, Vapor-Liquid Equilibria by UNIFAC Group Contribution.Revision and Extension.2, Ind.Eng.Chem.Process Des.Dev., 1982, 21, pp. 118-127.

Jacobson, Molecular Modeling Studies of Polymeric Transdermal Adhesives: Structure and Transport Mechanisms, Pharmaceutical Technology, Sep. 1999, pp. 120-.

Lee, et al, Microencapsulation of Fragrant Oil via in situ polymerization of pH and melamine-formaldehyde molar ratio, J.Microencapsulation, 2002, vol. 19, No. 5, pp. 559-569.

U.S. Appl. No. 10/718,368, filed Nov. 20, 2003, Popplewell et al.
U.S. Appl. No. 10/718,239, filed Nov. 20, 2003, Parekh et al.
U.S. Appl. No. 10/706,888, filed Nov. 13, 2003, Parekh et al.

X axis is fragrance Clog P
Y axis is minimum fragrance level (weight %)

X axis is solvent Clog P
Y axis is minimum solvent level (weight %)

X axis is surfactant level in product
Y axis is weight percent of encapsulated fragrance and solvent

ENCAPSULATED MATERIALS

STATUS OF RELATED APPLICATIONS

This application is a continuation-in-part of our earlier application, U.S. Ser. No. 10/718,240, filed on Nov. 20, 2003, the contents of which are hereby incorporated by reference as if set forth in its entirety.

FIELD OF THE INVENTION

The present invention is directed to a method for making capsules, and novel capsules containing fragrance materials. The capsules are well suited for use in personal care applications, laundry products and perfume and fragrance products.

BACKGROUND OF THE INVENTION

Encapsulation of fragrance and flavor materials is well known in the art. Encapsulation provides advantages to the fragrance/flavor product including the protection of the fragrance/flavor in the capsule core by a shell until the fragrance/flavor is intended to be delivered. In particular, capsules are often designed to deliver their contents at a desired time by the capsule shell being compromised at the desired time.

The capsule shell can be compromised by various factors such as temperature so that the contents are delivered when the capsule begins to melt. Alternatively the capsules can be compromised by physical forces, such as crushing, or other methods that compromise the integrity of the capsule. Additionally, the capsule contents may be delivered via diffusion through the capsule wall during a desired time interval.

It is obviously not desired that the core be released from the shell prematurely. Often, the capsule shell is somewhat permeable to the core contents when stored under certain conditions. This is particularly the case when many capsule types, such as those having aminoplast or cross-linked gelatin walls, are stored in aqueous bases, particularly those containing surfactants. In these cases, although the capsule shell is intact, the fragrance/flavor is removed from the core over time in a leaching process. The overall leaching mechanism may be viewed as a diffusion process, with transfer occurring from the capsule core to the aqueous media, followed by transfer to or solubilization into the surfactant micelles or vesicles. With normal surfactant concentrations of between 1 and 30% in consumer products, as compared to fragrance/flavor levels of 0.3 to 1%, it is clear that the partitioning favors absorption by the surfactant over time.

Bases that are primarily non-aqueous in nature, e.g., those that are based on alcohols, or volatile silicones can also leach fragrance/flavor from capsules over time. In these product types, the base solvent itself solubilizes the fragrance/flavor.

U.S. Pat. No. 6,106,875 discloses a method of encapsulating an amphiphilic volatile flavor or fragrance compound into a microcapsule have a hydrogel shell and an oil core. The flavor or fragrance compound in a liquid is transported into and solubilized into the core using water in the capsule wall to transport the material. The patent discloses that this technique provides a wall thickness and a flavor or fragrance concentration not previously obtainable.

Despite the above teaching and previous encapsulation technologies, there is an ongoing need to develop fragrance/flavor systems which are designed to retain the fragrance/flavor with minimal losses until it is needed and then be able to deliver the fragrance/flavor at the appropriate time.

SUMMARY OF THE INVENTION

It has been discovered that proper capsule core design can reduce and/or slow the effects of leaching of fragrance or flavor materials from the core. From this point forward the terms fragrance and flavor will be used interchangeably, and do not indicate a restriction of the invention in any way.

One embodiment of the invention is the use of a vast preponderance of fragrance materials with Clog P greater than 3.3, preferably greater than 4. In this embodiment of the invention greater than about 60 weight percent of the fragrance materials have a Clog P of greater than 3.3. In another highly preferred embodiment of the invention more than 80 weight percent of the fragrances have a Clog P value of greater than about 4.0. In the most preferred embodiment more than 90 weight percent of the fragrances have a Clog P value of greater than about 4.5.

Another embodiment is the use of significant levels of appropriate hydrophobic solvents in the fragrance core. Preferably greater than 30% of the core should consist of a hydrophobic solvent, and preferably that solvent should be selected from the group consisting of triglyceride oil, mono and diglycerides, mineral oil, silicone oil, polyalphaolefins, fatty alcohols, diethyl phthalate, and isopropyl myristate.

A third embodiment involves the use of hydrophobic polymers in the core to reduce leaching. Typically the core contains less than about 80 weight percent, preferably less than about 50 weight % and most preferably less than 20% weight percent hydrophobic polymer. Preferably the polymer is selected from the group consisting of ethyl cellulose, hydroxypropyl cellulose, cellulose acetate butyrate, ethylene vinyl acetate, polystyrene, and polyvinyl pyrrolidone and ester terminated polyamides or amide terminated polyamides.

In another embodiment the use of a vast preponderance of fragrance having Clog P greater than 3.3 is combined with the use of a significant level of appropriate hydrophobic solvent and/or hydrophobic polymer.

In another embodiment of the invention, since the capsule wall is permeable, it is possible for capsules containing a core of hydrophobic solvent, and/or high Clog P fragrance materials, to actually absorb fragrance materials from a fragrance containing base. This process can be improved via the initial inclusion of a more soluble solvent, which may be a lower Clog P fragrance material, in the core which partitions out of the core when placed in the base, thus providing free volume for fragrance material initially present in the base to occupy.

The migration of fragrance materials into the capsule also provides for the production of capsules by simply loading the capsules into a high concentration of fragrance material. The fragrance materials will preferably migrate into the core of the capsules. This allows an encapsulated fragrance to be manufactured by the selection of a permeable capsule material and hydrophobic core and immersing the capsules in a liquid system that contains a high fragrance loading.

Note that the invention is applicable to any encapsulation type provided that the shell wall is permeable to the desired actives. Thus, walls of aminoplasts, proteins, polyurethanes, polysaccharides, gums, celluloses, and any other encapsulating material may be used effectively in the present invention.

These and other embodiments of the present invention will be set forth in greater detail below.

DETAILED DESCRIPTION OF THE INVENTION

The Clog P of many perfume ingredients has been reported, for example, the Ponoma92 database, available from Daylight Chemical Information Systems, Inc. (Daylight CIS) Irvine, Calif. The values are most conveniently calculated using Clog P program also available from Daylight CIS. The program also lists experimentally determined logP values when available from the Pomona database. The calculated logP (Clog P) is normally determined by the fragment approach on Hansch and Leo (A. Leo, in Comprehensive Medicinal Chemistry, Vol. 4, C. Hansch, P. G. Sammens, J. B. Taylor and C. A. Ransden, Editiors, p. 295 Pergamon Press, 1990). This approach is based upon the chemical structure of the fragrance ingredient and takes into account the numbers and types of atoms, the atom connectivity and chemical bonding. The Clog P values which are most reliable and widely used estimates for this physiochemical property can be used instead of the experimental LogP values useful in the present invention. Further information regarding Clog P and logP values can be found in U.S. Pat. No. 5,500,138. It should be noted that the logP or Clog P normally referred to is the Octanol-Water partition coefficient. However, logP or Clog P values may also be defined for other Solvent-Water systems. These values are normally linearly related to the Octanol-Water logP or Clog P values. Thus, while the invention is described below in terms of the Octanol-Water partition coefficient, it should be recognized that it may be described using any desired Solvent-Water partition coefficient using an appropriate transformation.

Fragrance materials with lower logP or Clog P, these terms will be used interchangeably from this point forward throughout the specification, normally exhibit higher aqueous solubility. Thus, when these materials are in the core of a capsule which is placed in an aqueous system, they will have a greater tendency to diffuse into the base if the shell wall is permeable to the fragrance materials. Without wishing to be bound by theory, it is believed that normally the mechanism of leaching from the capsule proceeds in three steps in an aqueous base. First, fragrance dissolves into the water that hydrates the shell wall. Second, the dissolved fragrance diffuses through the shell wall into the bulk water phase. Third, the fragrance in the water phase is absorbed by the hydrophobic portions of the surfactant dispersed in the base, thus allowing leaching to continue. A similar process occurs in situations where the aqueous base does not contain a surfactant but rather a flavor absorbing lipid phase. The flavor absorbing lipid phases are found in a wide variety of food products such as mayonnaise, dressings, soups, baked goods, batters and the like. Lipids that could absorb flavors include but are not limited to soybean oil, corn oil, cottonseed oil, sunflower oil, lard, tallow and the like.

Figure 2:
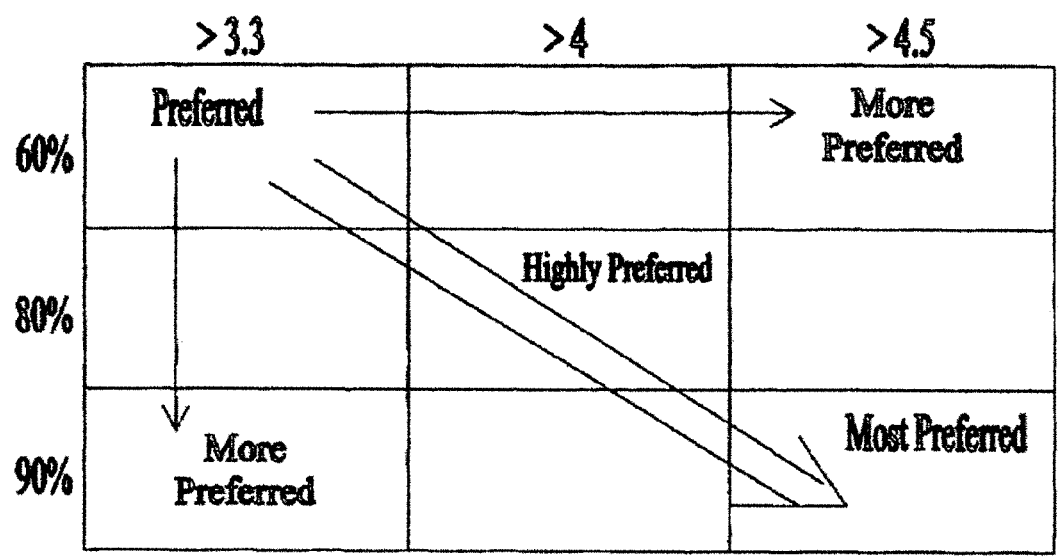
FIG. 2 is a schematic representation of the invention as embodied by the use of high Clog P fragrance materials.

This situation may be improved by one embodiment of the present invention which involves the use of a vast preponderance of high Clog P fragrance materials. In this embodiment of the invention greater than about 60 weight percent of the fragrance materials have a Clog P of greater than 3.3. In another highly preferred embodiment of the invention more than 80 weight percent of the fragrances have a Clog P value of greater than about 4.0. In the most preferred embodiment of the invention more than 90% of the fragrances have a Clog P value of greater than about 4.5. These embodiments are presented schematically, depicted with increasing preference in FIG. 2. Use of fragrance materials as described previously reduces the diffusion of fragrance through the capsule wall and into the base under specific time, temperature, and concentration conditions.

It should be noted that while Clog P and aqueous solubility are roughly correlated, there are materials with similar Clog P yet very different aqueous solubility. Clog P is the traditionally used measure of hydrophilicity in perfumery, and forms the basis for describing the invention. However, the invention may be further refined by the embodiment that greater than 60 weight percent of the fragrance materials have a Clog P of greater than 3.3 and a water solubility of less than 350 ppm. In another highly preferred embodiment of the invention more than 80 weight percent of the fragrances have a Clog P of greater than 4.0 and a water solubility of less than 100 ppm. In the most preferred embodiment of the invention more than 90% of the fragrances have a Clog P value of greater than about 4.5 and a water solubility of less than 20 ppm. In any case, selection of materials having a lower water solubility is preferred.

The following fragrance ingredients provided in Table I are among those suitable for inclusion within the capsule of the present invention:

TABLE 1

| PERFUME INGREDIENTS | CLOG P |
|---|---|
| Allyl cyclohexane propionate | 3.935 |
| Ambrettolide | 6.261 |
| Amyl benzoate | 3.417 |
| Amyl cinnamate | 3.771 |
| Amyl cinnamic aldehyde | 4.324 |
| Amyl cinnamic aldehyde dimethyl acetal | 4.033 |
| Iso-amyl salicylate | 4.601 |
| Aurantiol (Trade name for Hydroxycitronellal-methylanthranilate) | 4.216 |
| Benzyl salicylate | 4.383 |
| para-tert-Butyl cyclohexyl acetate | 4.019 |
| Iso butyl quinoline | 4.193 |
| beta-Caryophyllene | 6.333 |
| Cadinene | 7.346 |
| Cedrol | 4.530 |
| Cedryl acetate | 5.436 |
| Cedryl formate | 5.070 |
| Cinnamyl cinnamate | 5.480 |
| Cyclohexyl salicylate | 5.265 |
| Cyclamen aldehyde | 3.680 |
| Diphenyl methane | 4.059 |
| Diphenyl oxide | 4.240 |
| Dodecalactone | 4.359 |
| Iso E Super (Trade name for 1-(1,2,3,4,5,6,7,8-Octahydro-2,3,8,8-tetramethyl-2-naphthalenyl)-ethanone) | 3.455 |
| Ethylene brassylate | 4.554 |
| Ethyl undecylenate | 4.888 |
| Exaltolide (Trade name for 15-Hydroxyentadecanloic acid, lactone) | 5.346 |
| Galaxolide (Trade name for 1,3,4,6,7,8-Hexahydro-4,6,6,7,8,8-hexamethylcyclopenta-gamma-2-benzopyran) | 5.482 |
| Geranyl anthranilate | 4.216 |
| Geranyl phenyl acetate | 5.233 |
| Hexadecanolide | 6.805 |
| Hexenyl salicylate | 4.716 |
| Hexyl cinnamic aldehyde | 5.473 |
| Hexyl salicylate | 5.260 |
| Alpha-Irone | 3.820 |

TABLE 1-continued

| PERFUME INGREDIENTS | CLOG P |
|---|---|
| Lilial (Trade name for para-tertiary-Butyl-alpha-methyl hydrocinnamic aldehyde) | 3.858 |
| Linalyl benzoate | 5.233 |
| Methyl dihydrojasmone | 4.843 |
| Gamma-n-Methyl ionone | 4.309 |
| Musk indanone | 5.458 |
| Musk tibetine | 3.831 |
| Oxahexadecanolide-10 | 4.336 |
| Oxahexadecanolide-11 | 4.336 |
| Patchouli alcohol | 4.530 |
| Phantolide (Trade name for 5-Acetyl-1,1,2,3,3,6-hexamethyl indan) | 5.977 |
| Phenyl ethyl benzoate | 4.058 |
| Phenylethylphenylacetate | 3.767 |
| Phenyl heptanol | 3.478 |
| Alpha-Santalol | 3.800 |
| Thibetolide (Trade name for 15-Hydroxypentadecanoic acid, lactone) | 6.246 |
| Delta-Undecalactone | 3.830 |
| Gamma-Undecalactone | 4.140 |
| Vetiveryl acetate | 4.882 |
| Ylangene | 6.268 |

The higher Clog P materials are preferred, meaning that those materials with a Clog P value of 4.5 are preferred over those fragrance materials with a Clog P of 4; and those materials are preferred over the fragrance materials with a Clog P of 3.3.

The fragrance formulation of the present invention should have at least about 60 weight percent of materials with Clog P greater than 3.3, preferably greater than about 80 and more preferably greater than about 90 weight percent of materials with Clog P greater than 4.5.

Those with skill in the art appreciate that fragrance formulations are frequently complex mixtures of many fragrance ingredients. A perfumer commonly has several thousand fragrance chemicals to work from. Those with skill in the art appreciate that the present invention may contain a single ingredient, but it is much more likely that the present invention will comprise at least eight or more fragrance chemicals, more likely to contain twelve or more and often twenty or more fragrance chemicals. The present invention also contemplates the use of complex fragrance formulations containing fifty or more fragrance chemicals, seventy five or more or even a hundred or more fragrance chemicals in a fragrance formulation.

Preferred fragrance materials will have both high Clog P and high vapor pressure. Among those having these properties include: para cymene, caphene, mandarinal firm, Vivaldie™, terpinene, Verdox™, fenchyl acetate, cyclohexyl isovalerate, manzanate, myrcene, herbavert, isobutyl isobutyrate, tetrahydrocitral, ocimene and caryophyllene.

As described herein, the present invention is well suited for use in a variety of well-known consumer products such as laundry detergent and fabric softeners, liquid dish detergents, tumble dryer sheets, oral care products, personal care products, foodstuffs, beverages, automatic dish detergents, toothpastes, mouthwashs, as well as hair shampoos and conditioners. These products employ surfactant and emulsifying systems that are well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431,5,194,639, 4,968,451, 4,597,898, 4,561,998, 4,550,862, 4,537,707, 4,537,706, 4,515,705, 4,446,042, and 4,318,818. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Toothpastes and other oral care products that can employ the present invention include those described in U.S. Pat. Nos. 6,361,761, 6,616,915, 6,696,044, 6,193,956, 6,132,702, 6,004,538, 5,939,080, 5,885,554, 6,149,894, 5,505,933, 5,503,823, 5,472,685, 5,300,283 and 6,770,264.

Figure 3:
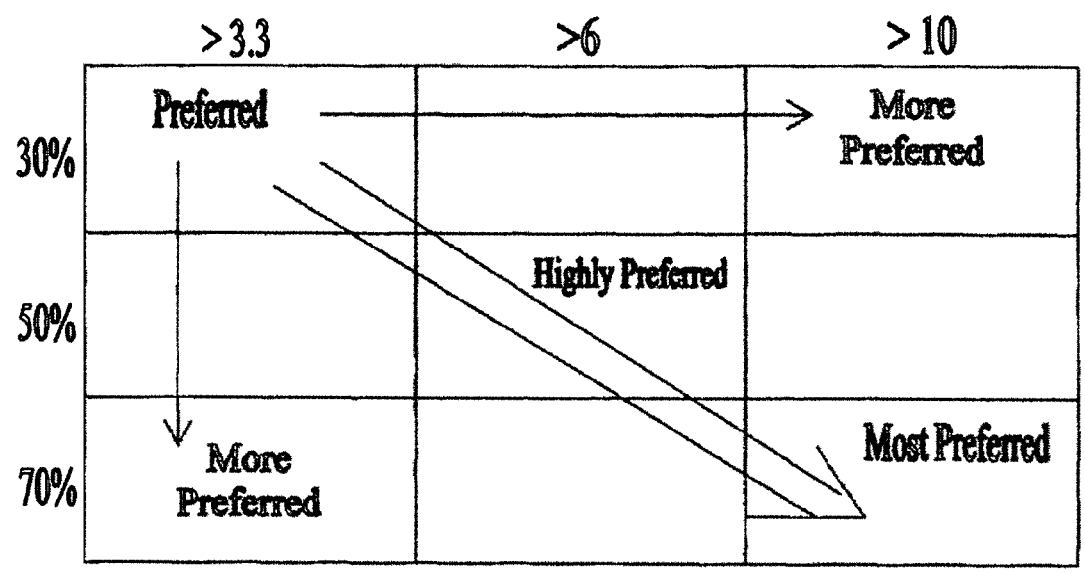
FIG. 3 is a schematic representation of the invention as embodied by the use of a significant level of hydrophobic solvent.

In addition to the fragrance materials that are to be encapsulated in the present invention, the present invention also contemplates the incorporation of solvent materials. The solvent materials are hydrophobic materials that are miscible in the fragrance materials used in the present invention. Suitable solvents are those having reasonable affinity for the fragrance chemicals and a Clog P greater than 3.3, preferably greater than 6 and most preferably greater that 10. These embodiments, including preferences of the invention are presented schematically in FIG. 3. Suitable materials include, but are not limited to triglyceride oil, mono and diglycerides, mineral oil, silicone oil, diethyl phthalate, polyalpa olefins, castor oil and isopropyl myristate. In a highly preferred embodiment the solvent materials are combined with fragrance materials that have high Clog P values as set forth above. It should be noted that selecting a solvent and fragrance with high affinity for each other will result in the most pronounced improvement in stability. This specific affinity may be measured by determining the Solvent-Water partition coefficient for the fragrance material. Appropriate solvents may be selected from the following non-limiting list:

Mono-, di- and tri-esters, and mixtures thereof, of fatty acids and glycerine. The fatty acid chain can range from $C_4$-$C_{26}$. Also, the fatty acid chain can have any level of unsaturation. For instance capric/caprylic triglyceride known as Neobee M5 (Stepan Corporation). Other suitable examples are the Capmul series by Abitec Corporation. For instance, Capmul MCM.

Isopropyl myristate

Fatty acid esters of polyglycerol oligomers:

R2CO—[OCH2-CH(OCOR1)-CH2O-]n, where R1 and R2 can be H or C4-26 aliphatic chains, or mixtures thereof, and n ranges between 2-50, preferably 2-30.

Nonionic fatty alcohol alkoxylates like the Neodol surfactants by BASF, the Dobanol surfactants by Shell Corporation or the BioSoft surfactants by Stepan. The alkoxy group being ethoxy, propoxy, butoxy, or mixtures thereof. In addition, these surfactants can be end-capped with methyl groups in order to increase their hydrophobicity.

Di- and tri-fatty acid chain containing nonionic, anionic and cationic surfactants, and mixtures thereof.

Fatty acid esters of polyethylene glycol, polypropylene glycol, and polybutylene glycol, or mixtures thereof.

Polyalphaolefins such as the ExxonMobil PureSym™ PAO line

Esters such as the ExxonMobil PureSym™ Esters

Mineral oil

Silicone oils such polydimethyl siloxane and polydimethylcyclosiloxane

Diethyl phthalate

Di-isodecyl adipate

The level of solvent in the core of the encapsulated fragrance material should be greater than about 30 weight percent, preferably greater than about 50 weight percent and most preferably greater than about 70 weight percent. In addition to the solvent it is preferred that higher Clog P fragrance materials are employed. It is preferred that greater than about 60 weight percent, preferably greater than 80 and more preferably greater than about 90 weight percent of the fragrance chemicals have Clog P values of greater than about 3.3, preferably greater than about 4 and most preferably greater than about 4.5. Those with skill in the art will appreciate that many formulations can be created employing various solvents and fragrance chemicals. The use of a high level of of high Clog P fragrance chemicals will likely require a lower level of hydrophobic solvent than fragrance chemicals with lower Clog P to achieve similar performance stability. As those with skill in the art will appreciate, in a highly preferred embodiment high Clog P fragrance chemicals and hydrophobic solvents comprise greater than about 80, preferably more than about 90 and most preferably greater than about 95 weight percent of the fragrance composition. As discussed above, specific Clog P values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

It has also been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymers may be selected from the non-limiting group below:

Copolymers of ethylene. Copolymers of ethylene and vinyl acetate (Elvax polymers by DOW Corporation). Copolymers of ethylene and vinyl alcohol (EVAL polymers by Kuraray). Ethylene/Acrylic elastomers such as Vamac polymers by Dupont.

Poly vinyl polymers, such as poly vinyl acetate.

Alkyl-substituted cellulose, such as ethyl cellulose (Ethocel made by DOW Corporation), hydroxypropyl celluloses (Klucel polymers by Hercules); cellulose acetate butyrate available from Eastman Chemical.

Polyacrylates. Examples being (i) Amphomer, Demacryl LT and Dermacryl 79, made by National Starch and Chemical Company, (ii) the Amerhold polymers by Amerchol Corporation, and (iii) Acudyne 258 by ISP Corporation.

Copolymers of acrylic or methacrylic acid and fatty esters of acrylic or methacrylic acid. These are side-chain crystallizing. Typical polymers of this type are those listed in U.S. Pat. Nos. 4,830,855, 5,665,822, 5,783,302, 6,255,367 and 6,492,462. Examples of such polymers are the Intelimer Polymers, made by Landec Corporation.

Polypropylene oxide.

Polybutylene oxide of poly(tetra hydrofuran).

Polyethylene terephthalate.

Polyurethanes (Dynam X by National Starch)

Alkyl esters of poly(methyl vinyl ether)-maleic anhydride copolymers, such as the Gantrez copolymers and Omnirez 2000 by ISP Corporation.

Carboxylic acid esters of polyamines. Examples of this are ester-terminated polyamide (ETPA) made by Arizona Chemical Company.

Poly vinyl pyrrolidone (Luviskol series of BASF).

Block copolymers of ethylene oxide, propylene oxide and/or butylenes oxide. These are known as the Pluronic and Synperonic polymers/dispersants by BASF.

Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

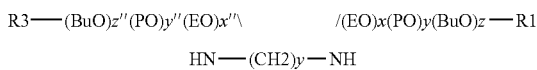

where R1, R2, R3, R4 is H or any alkyl of fatty alkyl chain group. Examples of such polymers are the commercially known as Tetronics by BASF Corporation.

We have also discovered that when capsules having cores containing a very large proportion of solvents with the appropriate Clog P values and/or with the high Clog P fragrance chemicals described above the encapsulated materials are actually capable of absorbing fragrance chemicals from surfactant-containing product bases. As is well appreciated by those with skill in the art, products such as, but not limited to fabric softeners, laundry detergents, toothpastes, bleaching products, shampoos and hair conditioners contain in their base formulas functional materials such as surfactants, emulsifying agents, detergent builders, whiteners, and the like along with fragrance chemicals. These products often aggressively absorb fragrance ingredients, most often due to the partially hydrophobic surfactant. Likewise, many food products contain high levels of fats and other lipids which also absorb flavors.

Most consumer products are made using an aqueous base containing a surfactant, although some products use glycols, polyhydric alcohols, alcohols, or silicone oils as the dominant solvent or carrier. Absorption from these bases is also possible if the core is properly designed and used at the appropriate level in the base. Examples of these products include many deodorants and anti-perspirents.

In the product base the fragrance is used to provide the consumer with a pleasurable fragrance during and after using the product or to mask unpleasant odors from some of the functional ingredients used in the product. As stated above, one long standing problem with the use of fragrance in product bases is the loss of the fragrance before the optimal time for fragrance delivery. We have discovered that with the proper selection of solvent and/or fragrance chemicals in the capsule core, and the proper level of core usage, the capsule will successfully compete for the fragrance chemicals present in the aqueous product base during storage. Eventually the core absorbs a significant quantity of fragrance, and finally an equilibrium level of fragrance is established in the core which is specific to the starting core composition and concentration in the base, type and concentration of the fragrance materials in the base, base composition (especially surfactant type and concentration), and conditions of storage. This ability to load the capsule core with fragrance material from the product base, particularly those product bases that contain a high concentration of surfactant clearly indicates that with judicious selection of core composition good fragrance stability within the core can be achieved.

Therefore, in an another embodiment of the present invention is a method for providing encapsulated fragrance products through the re-equilibration of the fragrance materials from the product base into the capsules. The process includes providing a product base containing fragrance materials and capsules with a permeable shell, the capsules containing a solvent as defined above or with high Clog P fragrance materials. The solvents and high Clog P fragrance materials have an affinity for the fragrance material. In order to absorb fragrance materials that previously are not present in the core of the capsules, to re-equilibrate into the capsule core it is preferred that the capsules contain some void space or contain some lower Clog P materials that can partition out of the capsule into product base. Capsule shells with the appropriate degree of permeability are described in the application.

As described above capsules loaded with solvent and or high Clog P fragrance materials will absorb other fragrance materials from the product. In this embodiment of the invention, the capsule cores compete with the surfactant and primarily aqueous media of the products for fragrance materials placed in the product bases during storage. Eventually the cores absorb a significant quantity of fragrance, and finally an equilibrium level of fragrance is established in the core which is specific to a given starting core composition and concentration in the base, type and concentration of fragrance materials in the base, base composition and conditions of storage. The self-loading of the cores in bases that have high concentrations of surfactants also indicates that by judicious core selection fragrance stability within the core can be achieved.

As used herein stability of the products is measured at room temperature or above over a period of at least a week. More preferably the capsules of the present invention are allowed to be stored at room temperature for more than about two weeks and preferably more than about a month.

More specifically, the present invention provides a method of encapsulating a fragrance material comprising:
  providing a product base containing non-encapsulated fragrance material and surfactant material;
  providing a permeable capsule wherein the permeable capsule contains greater than about 70 weight percent fragrance material having a Clog P value of greater than about 3.3 and/or suitable hydrophobic solvent; and
  allowing the non-encapsulated fragrance material and the permeable capsule material containing the fragrance material to come to equilibrium thereby transporting the non-encapsulated fragrance through the permeable shell wall into the interior of the capsule and retaining the fragrance contents of the permeable capsule.

In this embodiment of the invention a method for increasing the amount of a fragrance within a capsule comprising an aqueous base product that contains surfactant and fragrance, providing a capsule permeable to the fragrance when stored in the base, contained within said capsule greater than about 60 weight percent components selected from the group consisting of hydrophobic solvent and fragrance chemicals having a Clog P value of greater than about 3.3; storing the aqueous product base and the porous capsule for at least about a week, thereby allowing the fragrance chemicals provided in the aqueous base to be transported through the capsule wall. As further described, the selection of solvents and fragrance chemicals with correct Clog P values results in capsules with higher fragrance loading. The higher fragrance loading results in higher fragrance delivery than what was previously possible with fragrance provided in the aqueous base or provided in an oil included in the base. For example, when the capsules are employed in a fabric conditioner product it was discovered that the capsules of the present invention deposited fragrance as measured by the breaking of the capsules and the measurement of fragrance in the headspace to be more than 100% greater than fragrance alone or fragrance and solvent combinations deposited on the same cloth. In some instances the headspace measurement indicated an increase of more than 200 and even greater than about 300 percent when measuring fragrance in the headspace when employing the capsules with high Clog P materials and/or suitable solvents when compared to fragrance or fragrance solvent combinations.

In another embodiment of the present invention a sacrificial solvent is initially placed within the capsule. A sacrificial solvent is a solvent having a low Clog P value of less than about 3; generally from about 1 to about 2.75, preferably from about 1.25 to about 2.5, and most preferably from about 1.5 to about 2. If the Clog P of the sacrificial solvent is too low, the sacrificial solvents will be lost in the manufacture of the capsule materials. Suitable sacrificial solvents include benzyl acetate, and octanol. The level of sacrificial solvent used in the core should be greater than 10%, preferably greater than 20%, and most preferably greater than 30%. The remainder of the core is preferably composed of materials having a Clog P greater than 3.3, and more preferably greater than 4.0, and most preferably greater than 6.0.

The present invention provides a method of making capsules fragrance materials within the capsule comprising the steps of:
  providing a sacrificial solvent having a Clog P value of from about 1 to about 3 in the capsule core at a level of at least 10%;
  encapsulating the sacrificial solvent containing core with a permeable encapsulate material;
  providing the encapsulated sacrificial solvent containing core in a liquid environment containing fragrance materials;
  allowing the capsules containing the sacrificial solvent to come to equilibrium with the environment containing the high Clog P fragrance materials; whereby at least 20 weight percent of the sacrificial solvent migrates from the capsule into the environment.

Preferably more than 30 and more than 40 weight percent of the sacrificial solvent will migrate from the capsules to the environment, thereby allowing the capsules to increase the level of fragrance material inside the capsule by more than 10 weight percent, preferably more than 20 and most preferably more than 30 weight percent over the original weight of fragrance materials originally found inside the capsule.

Figure 5:
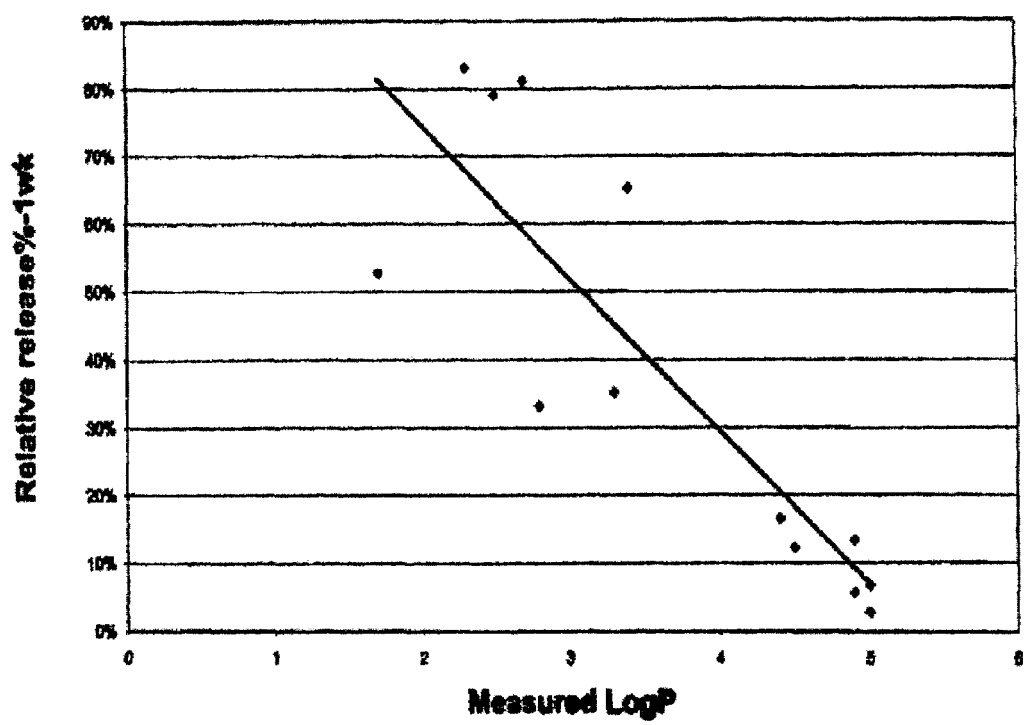
FIG. 5 is a graph of fragrance release over time versus the measured Clog P of the fragrances.

The time for this migration of the sacrificial solvent from the interior of the permeable capsule to the environment, thereby creating space within the capsule for the high Clog P materials to migrate into the capsule is as short as seven to ten days. A depiction of this effect is shown in FIG. 5 wherein low Clog P materials migrate more rapidly from the core than those materials with higher Clog P values. This means that under normal product manufacture, shipping and distribution, the sacrificial solvent will have sufficient time to migrate from the capsule interior, thereby creating free volume and allowing the preferred fragrance materials to migrate into the interior. Of course, longer periods of time will allow greater amounts of the sacrificial solvent to exit through the capsule wall and create more free volume and eventually a true equilibrium will occur where at a given temperature, the migration of sacrificial solvent out of the capsule and migration of fragrance material into the capsule will eventually end.

An important advantage of the migration technology is that capsules containing sacrificial solvent can be prepared in large quantities, and placed in various fragrance environments. This means that through the proper selection of fragrance materials, capsules and sacrificial solvent, encapsulated fragrance materials can be prepared without having to encapsulate each specific custom fragrance.

The present invention also contemplates the manufacture of intermediate products containing slurry with capsules containing highly hydrophobic cores with or without a sacrificial solvent. Intermediate products are those that are not sold to a consumer, but are used in the manufacturing process. In a preferred embodiment, the high Clog P solvent materials and/or fragrance materials could be encapsulated and provided as a slurry. To this, a quantity of non-encapsulated flavor or fragrance materials is added. The non-encapsulated or free flavor or fragrance molecules will preferentially migrate into the capsule and be retained within the capsule. Any sacrificial solvent present would permeate from the capsule, thereby creating a void within the capsule allowing more flavor or fragrance materials to partition into the capsule. This technique creates manufacturing efficiencies in that the sacrificial encapsulated solvents could be placed into an environment with free flavor or fragrance materials and then through the appropriate portioning effects, one would wind up with the desired encapsulated flavor or fragrance materials. Use of this technique would allow the use of suitable encapsulated solvent materials, and not require the encapsulation of each of the flavor or fragrance materials. This would be ideal for the preparation of intermediate products, those products containing flavors and fragrance capsules in an liquid environment, whereby the time in inventory would be advantageously used to allow for the portioning of the sacrificial solvent and flavor or fragrance materials. The liquid environment would preferably be an aqueous environment containing solvents or other additives which promote or accelerate fragrance transfer.

The invention in its various embodiments provides a capsule core composition that is able to retain a significant amount of fragrance within the capsule core and to deliver the higher level of fragrance contained therein at the desired time. We have discovered that the capsule products of the present invention under specified times of time, temperature, and concentration in various product bases retain more than about 10 weight percent, preferably more than 30 and most preferably more than 70 weight percent of the fragrance materials originally encapsulated.

As noted in the Summary of the Invention, the invention may be practiced with any permeable capsule wall material. Preferred encapsulating polymers include those formed from melamine-formaldehyde or urea-formaldehyde condensates, as well as similar types of aminoplasts. Additionally, capsules made via the simple or complex coacervation of gelatin are also preferred for use with the coating. Capsules having shell walls comprised of polyurethane, polyamide, polyolefin, polysaccaharide, protein, silicone, lipid, modified cellulose, gums, polyacrylate, polyphosphate, polystyrene, and polyesters or combinations of these materials are also functional.

Suitable polymers for encapsulation in the present invention include amino-based prepolymers such as urea-, melamine-, benzoguanamine-, and glycouril-formaldehyde resins and dimethyloldihydroxyethylene urea type prepolymers. These prepolymers can be used as blends and cross linkers with polyvinyl alcohol, polyvinyl amines, acrylates (acid functionality preferred), amines, polysaccharides, polyureas/urethanes, poly amino acids, and proteins. Other suitable polymers include polyesters, including biodegradable polyesters, polyamides, polyacrylates and polyacrylamides, polyvinyl polymer and copolymers with polyacrylates, polyurethanes, polyethers, polyureas, polycarbonates, naturally occurring polymers such as, polyanhydrides, polyphosphazines, polyoxazolines, and UV-cured polyolefins.

The present invention also contemplates the use of UV-cured versions of all the above polymer materials, epoxy-cross linked polyalcohols, polyamines, and polyurethanes/ureas, as well as multiple shell versions of the above.

Polymers systems are well know in the art and non-limiting examples of these include aminoplast capsules and encapsulated particles as disclosed in GB GB2006709 A; the production of micro-capsules having walls comprising styrene-maleic anhydride reacted with melamine-formaldehyde precondensates as disclosed in U.S. Pat. No. 4,396,670; an acrylic acid-acrylamide copolymer, cross linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules disclosed in EP 0 158 449 A1; etherified urea-formaldehyde polymer as disclosed in U.S. Pat. No. 5,204,185; melamine-formaldehyde microcapsules U.S. Pat. No. 4,525,520; cross linked oil-soluble melamine-formaldehyde precondensate U.S. Pat. No. 5,011,634; capsule wall material formed from a complex of cationic and anionic melamine-formaldehyde precondensates that are then cross linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; capsules composed of polymer or copolymer of styrene sulfonic acid in acid of salt form, and capsules cross linked with melamine-formaldehyde as disclosed in U.S. Pat. No. 4,001,140.

Capsule walls composed of negatively-charged, carboxyl containing polyelectrolyte with urea and formaldehyde are disclosed in U.S. Pat. No. 4,406,816. Capsule walls containing melamine-formaldehyde cross linked polymer or copolymer which possesses sulfonic acid groups as disclosed in WO 02/074430 A1.

Capsule walls comprising urea-formaldehyde or melamine-formaldehyde polymer and a second polymer comprising a polymer or copolymer of one or more anhydrides, preferably ethylene/maleic anhydride polymer as disclosed in U.S. Pat. No. 4,100,103; capsule walls contains melamine-formaldehyde precondensates and a polymer containing carboxylic acid groups as disclosed in EP 1 393 706 A1; encapsulated shell having an inner and outer surface as disclose in PCT 92/13448. Capsule walls comprising etherified amino-based prepolymers such as urea-, melamine-, benzoguanamine-, and glycouril-formaldehyde resins are known in the art.

Isocyanate-based capsule wall technology are disclosed in PCT 2004/054362; EP 0 148149 (also discloses polyamids, polyesters, polysulfonamide and polycarbonate capsules) EP 0 017 409 B1; U.S. Pat. No. 4,417,916, U.S. Pat. No. 4,124,526, U.S. Pat. No. 5,583,090, U.S. Pat. No. 6,566,306, U.S. Pat. No. 6,730,635, PCT 90/08468, PCT WO 92/13450, U.S. Pat. No. 4,681,806, U.S. Pat. No. 4,285,720 and U.S. Pat. No. 6,340,653.

Other suitable cross linking/chemistries are disclosed in U.S. Pat. No. 6,500,447; capsule walls containing free carboxyl groups having a polyamide, polyester structures and cross linked structures as disclosed in U.S. Pat. No. 4,946,624; wall material composed of materials that form microcapsules by coacervation techniques, preferably gelatin, cross linked preferably by glutaraldehyde as disclosed in U.S. Pat. No. 6,194,375 B1.

Other exemplary technologies include perfume materials absorbed in organic microparticles which have poly vinyl alcohol at their exterior. The particles are comprised of vinyl copolymers, styrenenic polymers, acrylic polymers and mixtures thereof, and cross linked versions thereof as disclosed in U.S. Pat. No. 3,726,803. A method to treat existing liquid-permeated capsule walls, wherein one component of a capsule wall treatment system comprising at least two components is held within the capsule wall material permeation pathways by being chemically complexed or otherwise bound therein as disclosed in PCT 03/020864.

Capsules having a continuous phase based on a mixture of an oil with a thermoplastic polymer and a discontinuous phase which is itself, and/or contains, a benefit agent and/or a colorant as disclosed in U.S. Pat. No. 6,740,631 B2.

An encapsulation process for multi-component controlled delivery systems for fabric care products are disclosed in U.S. Pat. No. 4,448,929. Wall comprising graft copolymer of polyvinyl alcohol and methyl vinyl ether/maleic acid as disclosed in U.S. Pat. Nos. 5,846,554 and 4,448,929.

Figure 4:
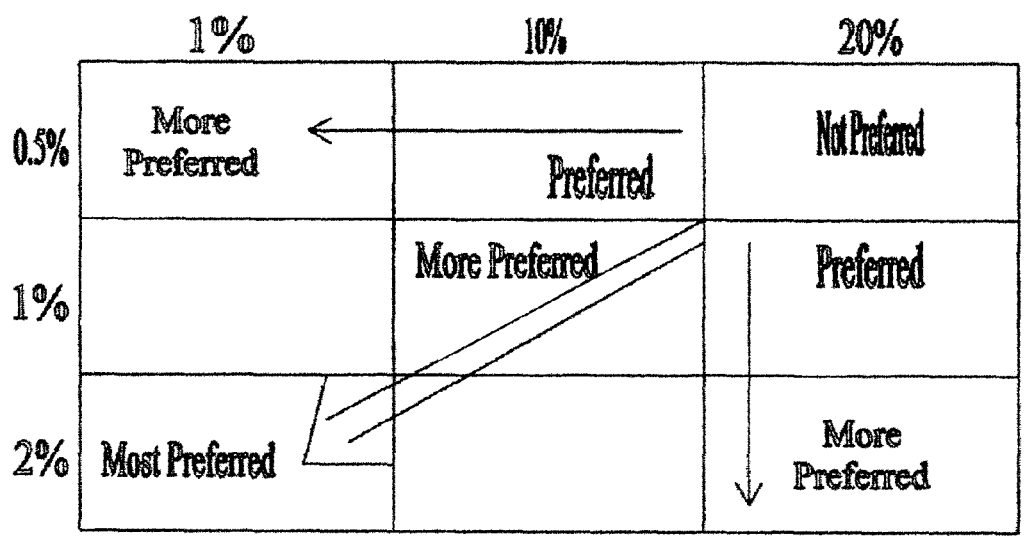
FIG. 4 is a schematic representation of the invention as embodied by the use of the product surfactant level.

Fragrances are normally added to the consumer product at a level of between about 0.2 and about 2 weight %. Surfactants are normally present at levels from about 1 to 30 weight %. In some instances the surfactant loading may be more than 85, typically more than 95 and greater than about 99 weight % of the formulated product such as in a tumble dryer sheet. We have discovered that when using the invention described above another factor provides improved stability. Use of a high level of total core (fragrance+solvent+polymer) compared to the surfactant level is preferred. Thus, a surfactant to core ratio of at most 20:1, preferably 10:1, and most preferably 3:1 should be used whenever possible. This embodiment of the invention is presented schematically in FIG. 4.

Suitable surfactant agents for use in the present invention include those surfactants that are commonly used in consumer products such as laundry detergents, fabric softeners and the like. The products commonly include cationic surfactants which also are used as fabric softeners; as well as non-ioinic and anionic surfactants.

Nonionic synthetic detergents are disclosed in U.S. Pat. No. 4,557,853, comprise a class of compounds which may be broadly defined as compounds produced by the condensation of alkylene oxide groups, hydrophilic in nature, with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with an hydrophobic base formed by the condensation of propylene oxide with propylene glycol. The hydrophobic portion of the molecule which, of course, exhibits water-insolubility has a molecular weight of from about 1500 to 1800. The addition of polyoxyethylene radicals to this hydrophobic portion tends to increase the water-solubility of the molecule as a whole and the liquid character of the products is retained up to the point where polyoxyethylene content is about 50% of the total weight of the condensation product.

Other suitable nonionic synthetic detergents include:

(i) The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 50 moles of ethylene oxide per mole of alkyl phenol. The alkyl substituent in such compounds may be derived from polymerized propylene, diisobutylene, octane, and nonane, for example.

(ii) Those derived from the condensation of ethylene oxide with the product resulting from the reaction of propylene oxide and ethylene diamine—products which may be varied in composition depending upon the balance between the hydrophobic and hydrophilic elements which is desired. Examples are compounds containing from about 40% to about 80% polyoxyethylene by weight and having a molecular weight of from about 5000 to about 11,000 resulting from the reaction of ethylene oxide groups with a hydrophobic base constituted of the reaction product of ethylene diamine and excess propylene oxide, said base having a molecular weight of the order of 2500 to 3000, are satisfactory.

(iii) The condensation product of aliphatic alcohols having from 8 to 18 carbon atoms, in either straight chain or branched chain configuration, with ethylene oxide, e.g., a coconut alcohol ethylene oxide condensate having from 10 to 50 moles of ethylene oxide per mole of coconut alcohol, the coconut alcohol fraction having from 10 to 14 carbon atoms.

(iv) Trialkyl amine oxides and trialkyl phosphine oxides wherein one alkyl group ranges from 10 to 18 carbon atoms and two alkyl groups range from 1 to 3 carbon atoms; the alkyl groups can contain hydroxy substituents; specific examples are dodecyl di(2-hydroxyethyl)amine oxide and tetradecyl dimethyl phosphine oxide.

Useful nonionic surfactants in the present invention are disclosed in U.S. Pat. No. 5,173,200 and include the condensation products of ethylene oxide with a hydrophobic polyoxyalkylene base formed by the condensation of propylene oxide with propylene glycol. The hydrophobic portion of these compounds has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product. Examples of compounds of this type include certain of the commercially-available Pluronic™ surfactants (BASF Wyandotte Corp.), especial those in which the polyoxypropylene ether has a molecular weight of about 1500-3000 and the polyoxyethylene contact is about 35-55% of the molecule by weight, i.e., Pluronic™ L-62.

Preferred nonionic surfactants include the condensation products of $C_8$-$C_{22}$ alkyl alcohols with 2-50 moles of ethylene oxide per mole of alcohol. Examples of compounds of this type include the condensation products of $C_{11}$-$C_{15}$ fatty alcohols with 3-50 moles of ethylene oxide per mole of alcohol which are commercially available from Shell Chemical Co., Houston, Tex., as, i.e., Neodol™ 23-6.5 ($C_{12}$-$C_{13}$ fatty alcohol condensed with about 7 moles of ethylene oxide), the PolyTergent™ SLF series from Olin Chemicals or the Tergitol™ series from Union Carbide, i.e., Tergitol™ S-15, which is formed by condensing about 15 moles of ethylene oxide with a $C_{11}$-$C_{15}$ secondary alkanol; Tergitol™ N-6, which is the condensation product of about 6 moles of ethylene oxide with isolauryl alcohol (CTFA name: isolaureth-6), Incropol™ CS-12, which is a mixture of stearyl and cetyl alcohol condensed with about 12 moles of ethylene oxide (Croda, Inc.) and Incropol™ L-7, which is lauryl alcohol condensed with about 7 moles of ethylene oxide (Croda, Inc.).

Preferred nonionic surfactants also include $C_8$-$C_{24}$ fatty acid amides such as the monoamides of a mixture of arachidic and behenic acid (Kenamide™ B, Humko Chem. Co., Memphis, Tenn.), and the mono- or di-alkanolamides of ($C_8$-$C_{22}$) fatty acids, such as the diethanol amide, monoethanol amide or monoisopropanolamide of coconut, lauric, myristic or stearic acid, or mixtures thereof. For example, Monamide™ S is the monoethanol amide of stearic acid (Mona Industries, Inc., Paterson, N.J.) and Monamide™ MEA is the monoethanol amide of coconut acid (Mona).

Other nonionic surfactants which may be employed include the ethylene oxide esters of ($C_6$-$C_{12}$) alkyl phenols such as (nonylphenoxy)polyoxyethylene ether. Particularly useful are the esters prepared by condensing about 8-12 moles of ethylene oxide with nonylphenol, such as the Igepal™. CO series (GAF Corp., New York, N.Y.).

Other useful nonionics include the ethylene oxide esters of alkyl mercaptans such as dodecyl mercaptan polyoxyethylene thioether, the ethylene oxide esters of fatty acids such as the lauric ester of polyethylene glycol, i.e., PEG 600 monostearate (Akzo Chemie) and the lauric ester of methoxypolyethylene glycol; the ethylene oxide ethers of fatty acid amides, the condensation products of ethylene oxide with partial fatty acid esters of sorbitol such as the lauric ester of sorbitan polyethylene glycol ether, and other similar materials, wherein the mole ratio of ethylene oxide to the acid, phenol, amide or alcohol is about 5-50:1.

U.S. Pat. No. 4,557,853 discloses suitable anionic surfactants suitable for use in the present invention. The most common type of anionic synthetic detergents can be broadly described as the water-soluble salts, particularly the alkali metal salts, of organic sulfuric reaction products having in the molecular structure an alkyl radical containing from about 8 to about 22 carbon atoms and a radical selected from the group consisting of sulfonic acid and sulfuric acid ester radicals. Important examples of these synthetic detergents are the sodium, ammonium or potassium alkyl sulfates, especially those obtained by sulfating the higher alcohols produced by reducing the glycerides of tallow or coconut oil; sodium or potassium alkyl benzene sulfonates, in which the alkyl group contains from about 9 to about 15 carbon atoms, especially those of the types described in U.S. Pat. Nos. 2,220,099 and 2,477,383, incorporated herein by reference; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about three moles of ethylene oxide; sodium or potassium salts of alkyl phenol ethylene oxide ether sulfates with about four units of ethylene oxide per molecule and in which the alkyl radicals contain about 9 carbon atoms; the reaction product of fatty acids esterified with isethionic acid and neutralized with sodium hydroxide where, for example, the fatty acids are derived from coconut oil; sodium or potassium salts of fatty acid amide of a methyl taurine in which the fatty acids, for example, are derived from coconut oil; and others known in the art, a number being specifically set forth in U.S. Pat. Nos. 2,486,921, 2,486,922 and 2,396,278.

Another broad class of surfactants are cationic, and can be referred to as quaternary amine salts, or "quats." These materials are described in U.S. Pat. No. 5,173,200, and also can function to condition the dried fabrics and to reduce static cling and lint adherence. The fabrics are softened in that their sheen, loft, and/or hand-feel is improved by either subjective or objective evaluation.

Subclasses of these materials are referred to by the art as monomethyl trialkyl quaternaries, imidazolinium quaternaries, dimethyl alkyl benzyl quaternaries, dialkyl dimethyl quaternaries, methyl dialkoxy alkyl quaternaries, diamido amine-based quaternaries and dialkyl methyl benzyl quaternaries wherein the "alkyl" moiety is preferably a ($C_8$-$C_{24}$) alkyl group and the quaternary (amine) is a chloride or methosulfate salt.

For convenience, one subclass of aliphatic quaternary amines may be structurally defined as follows:

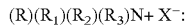

wherein R is benzyl, or lower(alkyl)benzyl; $R_1$ is alkyl of 10 to 24, preferably 12 to 22 carbon atoms; $R_2$ is $C_{10}$-$C_{.24}$-alkyl, $C_1$-$C_{14}$-alkyl, or ($C_{.2}$-$C_3$)hydroxyalkyl, $R_3$ is $C_1$-$C_4$-alkyl or ($C_2$-$C_3$)hydroxyalkyl and X represents an anion capable of imparting water solubility or dispersibility including chloride, bromide, iodide, sulfate and methosulfate. Particularly preferred species of these aliphatic quats include n-$C_{12}$-$C_{18}$-alkyl-dimethylbenzylammonium chloride (myrisalkonium chloride), n-$C_{.12}$-$C_{14}$-alkyldimethyl(ethylbenzyl)ammonium chloride (quaternium 14), dimethyl(benzyl)ammonium chloride, lauryl (trimethyl)ammonium chloride and mixtures thereof. These compounds are commercially available as the BTC series from Onyx Chemical Co., Jersey City, N.J. For example, BTC 2125M is a mixture of myrisalkonium chloride and quaternium-14. Dihydro-genated tallow methyl benzyl ammonium chloride is available as Variquat™ B-343 from Sherex Chem. Co., Dublin, Ohio.

Other useful aliphatic quats include those wherein both R and $R_1$ are ($C_8$-$C_{24}$)alkyl, such as the N,N-di-(higher)-$C_{10}$-$C_{.24}$-alkyl-N,N-di(lower)-C1-C4-alkyl-quaternary ammonium salts such as distearyl(dimethyl)ammonium chloride, dihydrogenated tallow(dimethyl)ammonium chloride, ditallow(dimethyl)ammonium chloride (Arquad™ 2HT-75, Akzo Chemie, McCook, Ill.), distearyl(dimethyl)ammonium methylsulfate and di-hydrogenated-tallow(dimethyl)ammonium methyl sulfate (Varisoft™ 137, Sherex).

Other useful quaternary ammonium antistatic agents include the acid salts of (higher(alkyl)-amido(lower)-alkyl)-dialkyl)-amines of the general formula:

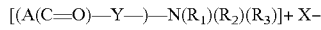

wherein A is a $C_{14}$-$C_{24}$ normal or branched alkyl group, Y is ethylene, propylene or butylene, $R_1$ and $R_2$ are individually H, $C_{.1}$-$C_{.4}$ (lower)alkyl or ($C_1$-$C_3$)hydroxyalkyl or together form the moiety—$CH_2$—$CH_2$ $YCH_2$—$CH_2$—, wherein Y is NH, O or $CH_2$; $R_3$ is the same as $R_1$ or is also [A(C=.O)Y—], and X is the salt of an organic acid. Compounds of this class are commercially available from Croda, Inc., New York, N.Y., as the Incromate™ series, e.g. Incromate™ IDL [isostearamidopropyl(dimethyl)amine lactate], Incromate™ISML [isostearamidopropy(morpholinium)lactate] and Incromate™ CDP [cocamidopropyl(dimethyl)amine propionate]. Ditallowdiamido methosulfate (quaternium 53) is available from Croda as Incrosoft™ T-75.

Preferred imidazolinium salts include: (methyl-1-tallowamido)ethyl-2-tallow imidazolinium methyl sulfate; available commercially from Sherex Chemical Co. as Varisoft™ 475; (methyl-1-oleylamido)ethyl-2-oleyl imidazolinium methyl sulfate; available commercial from Sherex Chemical Co., as Varisoft™ 3690, tallow imidazolinium methosulfate (Incrosoft™ S-75, Croda) and alkylimidazolinium methosulfate (Incrosoft™ CFI-75, Croda).

Other useful amine salts are the stearyl amine salts that are soluble in water such as stearyl-dimethylamine hydrochloride, distearyl amine hydrochloride, decyl pyridinium bromide, the pyridinium chloride derivative of the acetylaminoethyl esters of lauric acid, decylamine acetate and bis-[(oleoyl)-(5,8)-ethanoloxy]-tallow($C_{14}$-$C_{18}$)aminehydrogen phosphate (Necon™ CPS-100) and the like.

Although much of the description of the present invention has been direct to fragrance chemicals and fragrancing consumer products, the present invention is also advantageously used with encapsulated flavors as well. Those with skill in the art appreciate that oral care products such as toothpaste, gels, mouthwashes, mouth rinses, chewing gums and mouth sprays, as well as foodstuffs and beverages can also employ encapsulated flavor ingredients. The Clog P calculations set forth hereinabove for fragrance materials is also applicable for flavor materials. It is well appreciated by those with skill in the art that food grade materials are employed in the practice of the invention with encapsulated flavors. As used herein foodstuff is understood to mean The term "foodstuff" as used herein includes both solid and liquid ingestible materials for man or animals, which materials usually do, but need not, have nutritional value. Thus, foodstuffs include food products, such as, meats, gravies, soups, convenience foods, malt, alcoholic and other beverages, milk and dairy products, seafood, including fish, crustaceans, mollusks and the like, candies, vegetables, cereals, soft drinks, snacks, chewing gum, dog and cat foods, other veterinary products and the like.

Those with skill in the art appreciate that certain surfactants are employed in these food grade products. Surfactants include those described in U.S. Pat. No. 6,770,264 include those selected from the group consisting of anionic high-foam surfactants, such as linear sodium $C_{12-18}$ alkyl sulfates; sodium salts of $C_{12-16}$ linear alkyl polyglycol ether sulfates containing from 2 to 6 glycol ether groups in the molecule; alkyl-($C_{12-16}$)-benzene sulfonates; linear alkane-($C_{12-18}$)-sulfonates; sulfosuccinic acid mono-alkyl-($C_{12-18}$)-esters; sulfated fatty acid monoglycerides; sulfated fatty acid alkanolamides; sulfoacetic acid alkyl-($C_{12-18}$)-esters; and acyl sarcosides, acyl taurides and acyl isothionates all containing from 8 to 18 carbon atoms in the acyl moiety. Nonionic surfactants, such as ethoxylates of fatty acid mono- and diglycerides, fatty acid sorbitan esters and ethylene oxide-propylene oxide block polymers are also suitable. Particularly preferred surfactants are sodium lauryl sulfate and sacrosinate. Combinations of surfactants can be used.

Additional surfactant materials are described in U.S. Pat. No. 6,361,761 and include taurate surfactants The term "taurate surfactant" as used in the present specification is a surfactant which is a N-acyl N-alkyl taurate alkali metal salt. A preferred taurate surfactant is available from Finetex Inc., as Tauranol™ WHSP.

Representative taurate surfactants include the sodium, magnesium and potassium salts of N-cocoyl-N-methyltaurate, N-palmitoyl-N-methyl-taurate and N-oleyl-N-methyl taurate and their lauroyl, myristoyl, stearoyl, ethyl, n-propyl and n-butyl homologs.

In U.S. Pat. No. 6,696,044, sodium stearate is described as a preferred surfactants for use in chewing gum compositions. Sodium stearate is usually available as an approximate 50/50 mixture with sodium palmitate, and, a mixture of at least one citric acid ester of mono and/or diglycerides. A suitable example of a commercial stain removing agent in the latter class is IMWITOR 370.™ sold by Condea Vista Company. A further preferred surfactant is a mixture of lactic acid esters of monoglycerides and diglycerides.

U.S. Pat. No. 6,616,915 describe a broad class of surfactants suitable for use in oral hygiene. Typical examples of anionic surfactants are soaps, alkylbenzene sulphonates, alkane sulphonates, olefine sulphonates, alkylether sulphonates, glycerolether sulphonates, .alpha.-methylester sulphonates, sulphofatty acids, alkyl sulphates, fatty alcohol ether sulphates, glycerol ether sulphates, mixed hydroxy ether sulphates, monoglyceride (ether) sulphates, fatty acid amide (ether) sulphates, mono- and dialkyl sulphosuccinates, mono- and dialkyl sulfosuccinamates, sulpho triglycerides, amido soaps, ether carboxylic acids and their salts, fatty acid isethionates, fatty acid sarcosinates, fatty acid taurides, N-acylamino acids such as for example acyl lactylate, acyl tartrate, acyl glutamate and acyl aspartate, alkyl oligoglucoside sulphate, protein fatty acid condensate (especially plant products based on wheat) and alkyl (ether) phosphate. If the anionic surfactants contain polyglycol ether chains, these could show a conventional, but preferably a narrow homologue distribution. Typical examples of nonionic surfactants are fatty alcohol polyglycol ethers, alkylphenol polyglycol ethers, fatty acid polyglycol esters, fatty acid amide polyglycol ethers, fatty amino polyglycol ethers, alkoxylated triglycerides, mixed ethers, respectively mixed formals, possibly partially oxidilized alk(en)yl oligoglycosides, respectively glucoronic acid derivatives, fatty acid-N-alkylglucamides, protein hydrolysates (especially plant products based on wheat), polyol fatty acid esters, sugar esters, sorbitan esters, polysorbates and amine oxides. Provided that the nonionic surfactants contain polyglycolether chains, these can show a conventional, but preferably a narrow distribution of homologues. Based on application technology reasons—especially compatibility with the oral mucosa and foaming ability the use of alkyl sulphates, alkyl ether sulphates, monoglyceride (ether) sulphates, oleflne sulphonates and alkyl and/or alkenyl oligoglycosides as well as their mixtures is preferable, and they can be used as water containing pastes, preferably, however, as water free powders or granulates, which can be obtained for example by the Flash-Dryer or by the SKET procedure.

Conventional flavoring materials useful in flavoring products such as toothpastes and oral care products include saturated fatty acids, unsaturated fatty acids and amino acids; alcohols including primary and secondary alcohols, esters, carbonyl compounds including ketones, other than the dienalkylamides of our invention and aldehydes; lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillin, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimethoxy-phenol; amyl acetate; amyl cinnamate; γ-butyryl lactone; furfural; trimethylpyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methylpyrazine; tetramethylpyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; mono-potassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethylpyrazine; propyl-propenyl disulfide; propylpropenyl trisulfide; diallyl disulfide; diallyl trisulfide; dipropenyl disulfide; dipropenyl trisulfide; 4-methyl-2-[(methyl-thio)-ethyl]-1,3-dithiolane; 4,5-dimethyl-2-(methylthiomethyl)-1,3-dithiolne; and 4-methyl-2-(methylthiomethyl)-1,3-dithiolane. These and other flavor ingredients are provided in U.S. Pat. Nos. 6,110,520 and 6,333,180.

Fragrance retention within the capsule may be measured directly after storage at a desired temperature and time periods such as six weeks, two months, three months or more. The preferred manner is to measure total headspace of the product at the specified time and to compare the results to the headspace of a control product made to represent 0% retention via direct addition of the total amount of fragrance present. Alternatively, the product base may be performance tested after the storage period and the performance compared to the fresh product, either analytically or by sensory evaluation. This more indirect measurement often involves either measuring the fragrance headspace over a substrate used with the product, or odor evaluation of the same substrate.

Encapsulation of fragrances is known in the art, see for example U.S. Pat. Nos. 2,800,457, 3,870,542, 3,516,941, 3,415,758, 3,041,288, 5,112,688, 6,329,057, and 6,261,483. Another discussion of fragrance encapsulation is found in the Kirk-Othmer Encyclopedia. A preferred disclosure of fragrance encapsulation is found in U.S. Patent Applications, 2004/0142828 and 2004/0138093 both published during July, 2004.

After the fragrance material is encapsulated a cationically charged water-soluble polymer can be applied to the fragrance encapsulated polymer. This water-soluble polymer can also be an amphoteric polymer with a ratio of cationic and anionic functionalities resulting in a net total charge of zero and positive, i.e., cationic. Those skilled in the art would appreciate that the charge of these polymers can be adjusted by changing the pH, depending on the product in which this technology is to be used. Any suitable method for coating the cationically charged materials onto the encapsulated fragrance materials can be used. The nature of suitable cationically charged polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (co-valently) grafted to the capsule or particle surface. Chemical modification of the capsule or particle surface is another way to optimize anchoring of the polymer coating to capsule or particle surface. Furthermore, the capsule and the polymer need to want to go to the desired interface and, therefore, need to be compatible with the chemistry (polarity, for instance) of that interface. Therefore, depending on which capsule chemistry and interface (e.g., cotton, polyester, hair, skin, wool) is used the cationic polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from about 1,000 to about 1000,000,000, preferably from about 5,000 to about 10,000,000. As used herein molecular weight is provided as weight average molecular weight. Optionally, these cationic polymers can be used in combination with nonionic and anionic polymers and surfactants, possibly through coacervate formation.

A more detailed list of cationic polymers that can be used to coat the encapsulated fragrance is provided in co-pending commonly assigned U.S. Patent Applications, 2004/0142828 and 2004/0138093 both published during July, 2004.

Polysaccharides such as guar, alginates, starch, xanthan, chitosan, cellulose, dextrans, arabic gum, carrageenan, hyaluronates. These polysaccharides can be employed with:

(a) cationic modification and alkoxy-cationic modifications, such as cationic hydroxyethyl, cationic hydroxy propylas commercially available as Celquat L-200 (Polyquaternium-4), Polyquaternium-10 and Polyquaternium-24, from National Starch, Bridgewater, N.J.;

(b) aldehyde, carboxyl, succinate, acetate, alkyl, amide, sulfonate, ethoxy, propoxy, butoxy, and combinations of these functionalities; and (c) any hydrophobic modification (compared to the polarity of the polysaccharide backbone).

The above modifications described in (a), (b) and (c) can be in any ratio and the degree of functionalization up to complete substitution of all functionalizable groups, and as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified than the backbone. The counter ions can be any halide ion or organic counter ion. U.S. Pat. No. 6,297,203 and U.S. Pat. No. 6,200,554.

Another source of cationic polymers contain protonatable amine groups so that the overall net charge is zero (amphoteric: mixture of cationic and anionic functional groups) or positive. Examples are silk protein, zein, gelatin, keratin, collagen and any polypeptide, such as polylysine.

Further cationic polymers include poly vinyl polymers, such as i.e. poly vinyl amine and its copolymers with N-vinyl formamide, known as Lupamin 9095 from BASF Corporation. Further suitable cationic polymers containing hydroxy alkyl vinyl amine units, as disclosed in U.S. Pat. No. 6,057,404.

Another class of materials are polyacrylates with the polymers of choice are those containing the cationic monomer dimethylaminoethyl methacrylate (DMAEMA) or methacrylamidopropyl trimethyl ammonium chloride (MAPTAC). DMAEMA can be found in Gafquat and Gaffix VC-713 polymers from ISP. MAPTAC can be found in BASF's Luviquat PQ11 PN and ISP's Gafquat HS100.

Another group of polymers that can be used are those that contain cationic groups in the main chain or backbone. Included in this group are:

(1) polyalkylene imines such as polyethylene imine, commercially available as Lupasol from BASF. Any molecular weight and any degree of crosslinking of this polymer can be used in the present invention;

(2) ionenes having the general formula set forth as —[N(+)R1R2-A1-N(R5)-X—N(R6)-A2-N(+)R3R4-A3]n-2Z-, as disclosed in U.S. Pat. No. 4,395,541 and U.S. Pat. No. 4,597,962;

(3) adipic acid/dimethyl amino hydroxypropyl diethylene triamine copolymers, such as Cartaretin F-4 and F-23, commercially available from Sandoz;

(4) polymers of the general formula —[N(CH3)2-(CH2)x-NH—(CO)—NH—(CH2)y—N(CH3)2)-(CH2)z-O—(CH2)p]n-, with x, y, z, p=1-12, and n according to the molecular weight requirements. Examples are Polyquaternium 2 (Mirapol A-15), Polyquaternium-17 (Mirapol AD-1), and Polyquaternium-18 (Mirapol AZ-1).

Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e. Polyquaternium-80). Examples of suitable polysiloxanes are found in U.S. Pat. Nos. 4,395,541 4,597,962 and U.S. Pat. No. 6,200,554. Another group of polymers that can be used to improve capsule/particle deposition are phospholipids that are modified with cationic polysiloxanes. Examples of these polymers are found in U.S. Pat. No. 5,849,313; PCT Patent Application 9518096A1 and European Patent EP0737183B1.

Furthermore, copolymers of silicones and polysaccharides and proteins can be used and are commercially available Crodasone Series.

Another class of polymers include polyethylene oxide-co-propyleneoxide-co-butylene oxide polymers of any ethylene oxide/propylene oxide/butylene oxide ratio with cationic groups resulting. Examples of such polymers are the commercially available TETRONIC brand polymers.

Suitable polyheterocyclic (the different molecules appearing in the backbone) polymers include the piperazine-alkylene main chain copolymers disclosed in *Ind. Eng. Chem. Fundam.*, (1986), 25, pp. 120-125, by Isamu Kashiki and Akira Suzuki.

Also suitable for use in the present invention are copolymers containing monomers with cationic charge in the primary polymer chain. Up to 5 different types of monomers may be used. Any co-monomer from the types listed in this specification may also be used. Examples of such polymers are poly diallyl dimethyl ammonium halides (PolyDADMAC) copolymers of DADMAC with vinyl pyrrolidone, acrylamides, imidazoles, imidazolinium halides, etc. These polymers are disclosed in Henkel EP0327927A2 and PCT Patent Application 01/62376A1. Also suitable are Polyquaternium-6 (Merquat 100), Polyquaternium-7 (Merquats S, 550, and 2200), Polyquaternium-22 (Merquats 280 and 295) and Polyquaternium-39 (Merquat Plus 3330), available from Ondeo Nalco.

Substantivity of these polymers may be further improved through formulation with cationic, amphoteric and nonionic surfactants and emulsifiers, or by coacervate formation between surfactants and polymers or between different polymers. Combinations of polymeric systems, (including those mentioned previously, may be used for this purpose as well as those disclosed in EP1995/000400185.

Furthermore, polymerization of the monomers listed above into a block, graft or star (with various arms) polymers can often increase the substantivity toward various surfaces. The monomers in the various blocks, graft and arms can be selected from the various polymer classes listed in this specification.

Polymers that are known as deposition aids, and in a preferred embodiment are also cationic can be found in the following resources:

Encyclopedia of Polymers and Thickeners for Cosmetics, Robert Lochhead and William From, in Cosmetics & Toiletries, Vol. 108, May 1993, pp. 95-138;

*Modified Starches: Properties & Uses*, O. B. Wurzburg, CRC Press, 1986. Specifically, Chapters 3, 8, and 10;

U.S. Pat. Nos. 6,190,678 and 6,200,554; and PCT Patent Application WO 01/62376A1 assigned to Henkel.

The preferred cationically charged materials are selected from the group consisting of cationically modified starch and cationically modified guar, polymers comprising poly diallyl dimethyl ammonium halides (PolyDADMAC), and copolymers of DADMAC with vinyl pyrrolidone, acrylamides, imidazoles, imidazolinium halides, and the like. For instance, Polyquaternium-6, 7, 22 and 39, all available from Ondeo Nalco.

The preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc.

The preferred cationic guar has a molecular weight of from about 50,000 to about 5,000,000. The preferred cationic guar products are Jaguar C-162 and Jaguar C-17 and are commercially available from Rhodia Inc.

The level of cationic polymer is from about 1% to about 3000%, preferably from about 5% to about 1000% and most preferably from about 10% to about 500% of the fragrance containing compositions, based on a ratio with the fragrance on a dry basis.

The weight ratio of the encapsulating polymer to fragrance is from about 1:25 to about 1:1. Preferred products have had the weight ratio of the encapsulating polymer to fragrance varying from about 1:10 to about 4:96.

For example, if a capsule blend has 20 weight % fragrance and 20 weight % polymer, the polymer ratio would be (20/20) multiplied by 100 (%)=100%.

Preferred encapsulating polymers include those formed from melamine-formaldehyde or urea-formaldehyde condensates, as well as similar types of aminoplasts. Additionally, capsules made via the simple or complex coacervation of gelatin are also preferred for use with the coating. Capsules having shell walls comprised of polyurethane, polyamide, polyolefin, polysaccaharide, protein, silicone, lipid, modified cellulose, gums, polyacrylate, polyphosphate, polystyrene, and polyesters or combinations of these materials are also functional.

A representative process used for aminoplast encapsulation is disclosed in U.S. Pat. No. 3,516,941 though it is recognized that many variations with regard to materials and process steps are possible. A representative process used for gelatin encapsulation is disclosed in U.S. Pat. No. 2,800,457 though it is recognized that many variations with regard to materials and process steps are possible. Both of these processes are discussed in the context of fragrance encapsulation for use in consumer products in U.S. Pat. Nos. 4,145,184 and 5,112,688, respectively.

Particle and capsule diameter can vary from about 10 nanometers to about 1000 microns, preferably from about 50 nanometers to about 100 microns and is most preferably from about 2 to about 15 microns. The capsule distribution can be narrow, broad, or multi-modal. Multi-modal distributions may be composed of different types of capsule chemistries.

Well known materials such as solvents, surfactants, emulsifiers, and the like can be used in addition to the polymers described above to encapsulate the fragrance without departing from the scope of the present invention. It is understood that the term encapsulated is meant to mean that the fragrance material is substantially covered in its entirety. Encapsulation can provide pore vacancies or interstitial openings depending on the encapsulation techniques employed. More preferably the entire fragrance material portion of the present invention is encapsulated.

In the present invention, the encapsulated fragrance is well suited for wash-off products. Wash-off products are understood to be those products that are applied for a given period of time and then are removed. These products are common in areas such as laundry products, and include detergents, fabric conditioners, and the like; as well as personal care products which include shampoos, hair rinses, body washes, soaps, toothpastes and the like.

As described herein, the present invention is well suited for use in a variety of well-known consumer products such as laundry detergent and fabric softeners, liquid dish detergents, automatic dish detergents, as well as hair shampoos and conditioners. These products employ surfactant and emulsifying systems that are well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, 4,424,134. Liquid dish detergents are described in U.S. Pat. Nos. 6,069,122 and 5,990,065; automatic dish detergent products are described in U.S. Pat. Nos. 6,020,294, 6,017, 871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929, 022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Toothpastes and oral care compositions that can employ the present invention include U.S. Pat. Nos. 6,361, 761, 6,616,915, 6,696,044, 6,193,956, 6,132,702, 6,004,538, 5,939,080, 5,885,554, 6,149,894, 5,505,933, 5,503,823, 5,472,685, 5,300,283 and 6,770,264. Other consumer products include personal care products including but not limited to lotions, creams, hair gels, anti-persperants, shaving products, colognes, and bodywashes.

Improved fragrance performance includes longer lasting fragrance, improved substantivity of the fragrance on cloth or the ability to provide improved fragrance notes, such as specific fragrance notes through the use of the present invention.

While the above description is primarily to fabric rinse conditioner products, additional studies for shampoos, detergent and other cleaning products have also led to preferred embodiments for these products as well.

While the preferred coating materials may be simply dissolved in water and mixed with a suspension of capsules prior to addition to the final product, other modes of coating use and application are also possible. These modes include drying the coating solution in combination with the capsule suspension for use in dry products such as powder detergents, or using higher concentrations of coating such that a gel structure is formed, or combining the coating material with other polymers or adjuvants which serve to improve physical characteristics or base compatibility. Drying or reducing the water content of the capsule suspension prior to coating addition is also possible, and may be preferable when using some coating materials. Further, when using some coating materials it is possible to add the coating to the application base separately from the encapsulated fragrance.

Solvents or co-solvents other than water may also be employed with the coating materials. Solvents that can be employed here are (i) polyols, such as ethylene glycol, propylene glycol, glycerol, and the like, (ii) highly polar organic solvents such as pyrrolidine, acetamide, ethylene diamine, piperazine, and the like, (iii) humectants/plasticizers for polar polymers such as monosaccharides (glucose, sucrose, etc.), amino acids, ureas and hydroxyethyl modified ureas, and the like, (iv) plasticizers for less polar polymers, such as diisodecyl adipate (DIDA), phthalate esters, and the like.

The coating polymer(s) may also be added to a suspension of capsules that contain reactive components such that the coating becomes chemically (covalently) grafted to the capsule wall, or the coating polymer(s) may be added during the crosslinking stage of the capsule wall such that covalent partial grafting of the coating takes place.

The present invention also includes the incorporation of a silicone or a siloxane material into a product that contains encapsulated fragrances of the present invention. As used herein silicone is meant to include both silicone and siloxane materials. Also included in the definition of silicone materials are the cationic and quaternized of the silicones. These materials are well known in the art and include both linear and branched polymers.

In addition to silicones, the present invention also includes the use of mineral oils, triglyceride oils and sucrose polyester materials in a similar matter as the silicone materials. For brevity, these materials are understood to be included in the term silicone as used in this specification unless noted to the contrary. Those with skill in the art will also appreciate that it is possible to incorporate a silicone in combination with mineral oils and the like in carrying out the present invention.

The silicone material is preferably admixed to the encapsulated fragrance-containing product after the fragrance materials are encapsulated. Optionally, the silicone material may be mixed directly with the product base either before or after the encapsulated fragrance has been added.

Suitable silicone materials include amodiemthicone, polymethylalkyl siloxanes, polydimethylalkyl siloxanes, dimethicone, dimethicone copolyol, dimethiconol, disiloxane, cyclohexasiloxane, cyclomethicone, cyclopentasiloxane, phenyl dimethicone, phenyl trimethicone, silicone quaternarary materials including silicone quaternium-8, and silicone quaternium-12, trimethylsiloxyamidodimethicone, trimethylsiloxysilicate and the like. These materials are commercially well known materials and are available from suppliers such as Dow Corning, Shin-Etsu, Wacker Silicones Corporation and the like. The preferred silicon is Dow Corning 245 Fluid (Dow Corning, Midland Mich.), which is described as containing greater than about 60 weight percent decamethylcyclopentasiloxane and less than or equal to about 4 weight percent dimethylcyclosiloxanes.

Amino functional silicone oils such as those described in U.S. Pat. Nos. 6,355,234 and 6,436,383 can also be advantageous employed.

Capsules made via various methods, including melamine-formaldehyde polymerization, urea-formaldehyde polymerization, melamine-formaldehyde cross-linking of suitable polymers, and urea-formaldehyde cross-linking of suitable polymers are permeable to fragrance molecules when placed in aqueous surfactant dispersions typical of consumer product bases. Fragrance molecules thus leach from the core of the capsule to the external base, resulting in a decline of performance over time.

Figure 1:
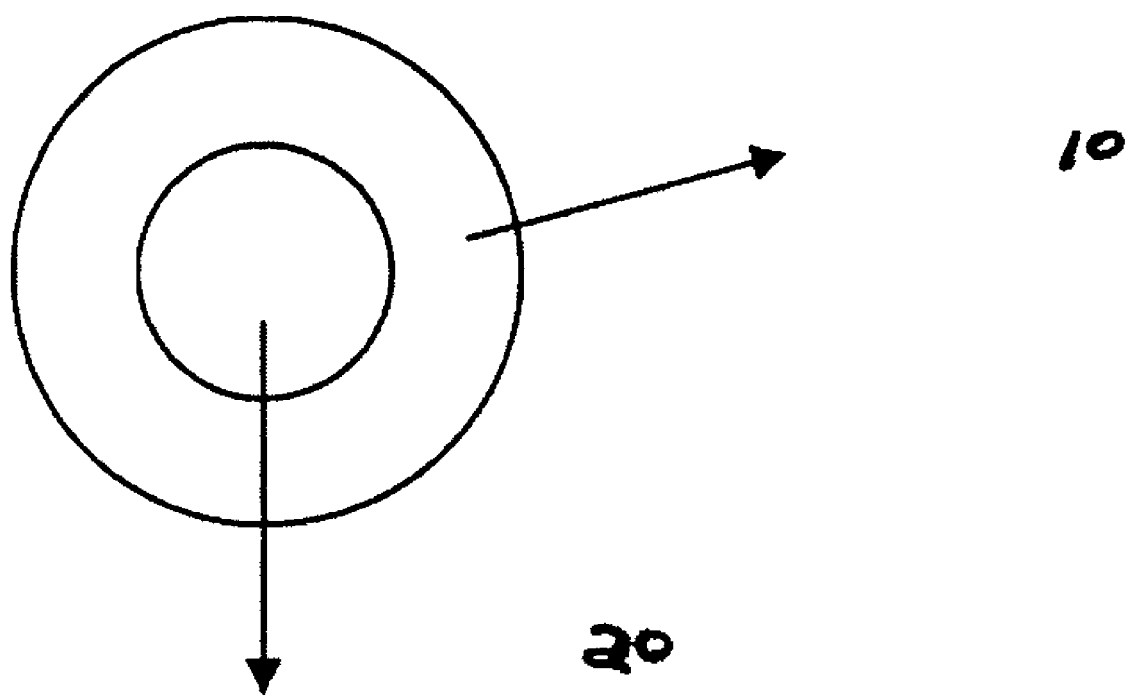
FIG. 1 is a cross sectional drawing of the particle.

Those with skill in the art will appreciate that the diffusion of the fragrance material will depend on various factors including the selection of the fragrance materials, the encapsulating polymer, the surfactant level found in the product, and the physical parameters of the encapsulated particles. By physical properties it is meant such factors such as the thickness of the core, the thickness of the shell, and the relative diameter of the particles. Referring to FIG. 1, a simplified depiction of the shell wall of the particle 10 and the core 20 containing the fragrance and solvent stabilizer is depicted. Those with skill in the art will appreciate that other depcitions of the encapsulated fragrance are possible, which include other features such as optional secondary coatings on the shell wall, which are not depicted for purposes of clarity.

In order to demonstrate the invention, the following examples were conducted. All U.S. patent and patent applications referenced herein, are hereby incorporated by reference as if set forth in their entirety. The following disclosures are provided to exemplify the present invention.

Unless noted to the contrary all weights are weight percent and all fragrance chemicals used herein are available from International Flavors & Fragrances Inc., New York, N.Y. Upon review of the foregoing, numerous adaptations, modifications and alterations will occur to the reviewer. These adaptations, modifications, and alterations will all be within the spirit of the invention. Accordingly, reference should be made to the appended claims in order to ascertain the scope of the present invention.

EXAMPLE 1

Cationic polymer-coated capsules were prepared by mixing uncoated fragrance-containing capsules with the cationic polymeric deposition aid at the desired level. This mixing can be done during the manufacturing process of the capsules or by post-addition of the cationic deposition aid as a solution. The uncoated capsules were prepared by interfacial polymerization of fragrance droplets. To make the capsule slurry, a copolymer of acrylamide and acrylic acid was first dispersed in water together with a methylated melamine-formaldehyde resin. These two components were allowed to react under acidic conditions. Fragrance was then added into the solution and droplets of the desired size were achieved by high shear homogenization. Curing of the polymeric layer around the fragrance droplets was achieved by increasing the temperature to 50-85° C.

EXAMPLE 2

A slurry of capsules having shell walls composed of an acrylamide-acrylic acid co-polymer cross-linked with melamine-formaldehyde resin as described in Example 1 was mixed with a concentrated fabric conditioner. The fabric conditioner was commercially obtained and did not contain fragrance. The capsule slurry contained approximately 25 weight % fragrance, and approximately 10% shell-wall material. The level of fragrance added to the product was 0.8%, and leaching was followed by headspace measurement via Solid Phase Microextraction (SPME).

Figure 6:
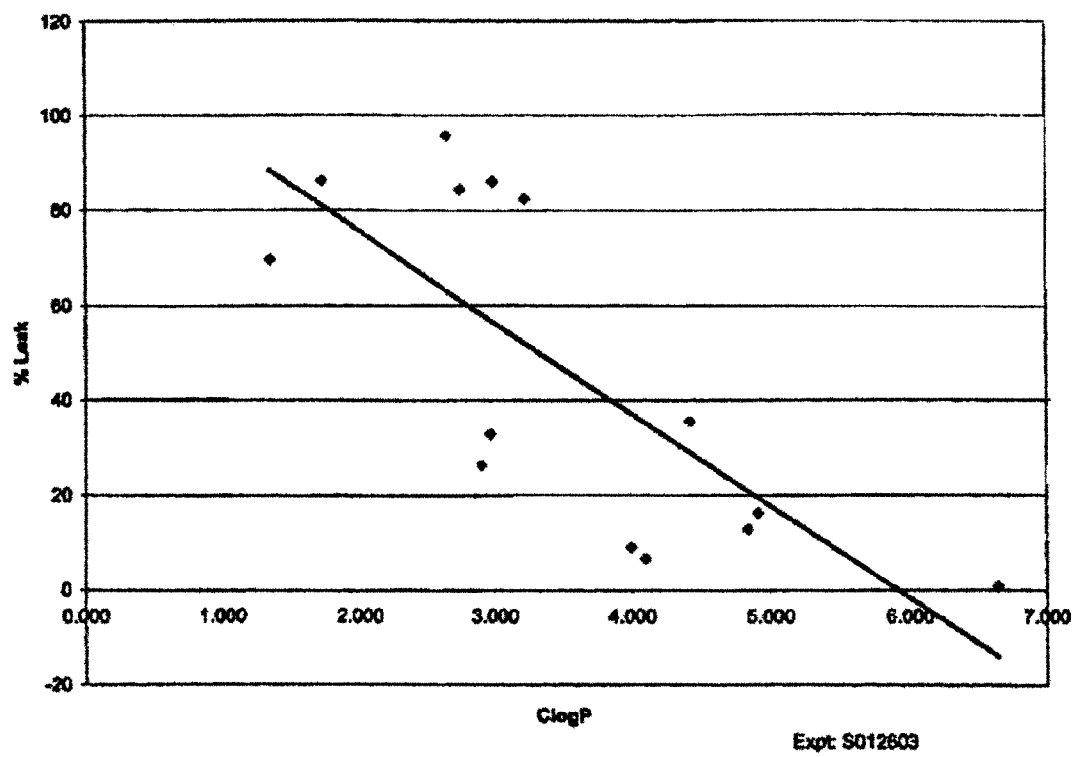
FIG. 6 is a graph of fragrance release over time versus the Clog P of the fragrance in a fabric softener.

As can be seen from FIG. 6, after storage at ambient temperature for six weeks, the release of fragrance materials is inversely related to Clog P.

The fragrance used in Examples 1 and 2 above was comprised of equal weight percents of the following fragrance materials:

Ethyl-2-methyl valerate (manzanate); limonene, DH myrcenol, phenyl ethyl alcohol, benzyl acetate, geraniol, dimethyl benzyl carbonate acetate, methyl nonyl acetaldehyde, cyclacet, methoxy naphthalene (yara yara), beta ionone, lilial, hexyl salicylate and tonalid.

EXAMPLE 3

A slurry of capsules having shell walls composed of an acrylamide-acrylic acid co-polymer cross-linked with melamine-formaldehyde resin was mixed with a commercially obtained concentrated fabric conditioner (DOWNY, Procter & Gamble). The capsules slurry contained fragrance levels as noted below, and approximately 10% shell-wall material. The level of fragrance added to the product was 0.8%, and leaching was followed by headspace measurement via Solid Phase Microextraction (SPME). The fragrance used consisted of either Lilial (logP=4.4, slurry level=14%) or Cyclacet (logP=3.3, slurry level=24%).

The DOWNY (Procter & Gamble, Cincinnati, Ohio) fragrance free fabric softener was purchased form a local grocery store and contained approximately 25% cationic surfactants as the active. As can be seen from the table below, after storage at ambient temperature, for up to five weeks at ambient temperature, the released level of Lilial was low and relatively constant, while that of Cyclacet was high and increasing.

|  | 1 week | % Free fragrance 2 weeks | 5 weeks |
| --- | --- | --- | --- |
| Lilial capsule | 3 | 2 | 12 |
| Cyclacet capsule | 62 | 72 | 87 |

EXAMPLE 4

A slurry of capsules having shell walls composed of an acrylamide-acrylic acid co-polymer cross-linked with melamine-formaldehyde resin made as described above was mixed with a model shampoo base. The capsule slurry contained fragrance levels as noted below, and approximately 10% shell-wall material. The level of fragrance added to the product was 0.8%, and leaching was followed by headspace measurement via Solid Phase Microextraction (SPME). The fragrance used consisted of either Lilial (logP=4.4, slurry level=14%) or Cyclacet (logP=3.3, slurry level=24%).

The shampoo base had an anionic surfactant as the main active with a concentration of 10% and contained sodium laureth (3) sulfate.

Other ingredients in the shampoo included Cocoamido propyl betaine, MEA amides, solvents, conditioning agents (silicone, cationic polymer, etc), etc.

As can be seen from the table below, after storage at ambient temperature for up to six weeks at ambient temperature, the released level of Lilial was low and relatively constant, while that of Cyclacet was high and increased over time.

| Shampoo Base | 1 week | % Free fragrance 3 weeks | 6 weeks |
|---|---|---|---|
| Lilial | 5 | 7 | 14 |
| Cyclacet | 32 | 105 | 91 |

This Example demonstrates that despite the different bases and different nature of the ingredients in each base in Examples 3 and 4, the Lilial capsule was consistently better than the Cyclacet capsule.

EXAMPLE 5

A slurry of NEOBEE M5 oil [Stephan Company, Northfield, Ill.]-containing capsules (35% level) having shell walls composed of an acrylamide-acrylic acid co-polymer crosslinked with melamine-formaldehyde resin was mixed with a fabric softener base containing 0.2% of a model fragrance accord. A lab made fabric softener base was used which contained approximately 9% quaternary amine as the primary active. The slurry was not added to the control product. Both samples were adjusted to have the same concentration of fabric softener actives. The level of Neobee M5 used (encapsulated) in the base was 5%. The two samples s were aged for 2 weeks at 40° C. and then used to rinse cloth swatches in an identical lab bench test. The fabrics were air dried and the headspace of an equal mass of fabrics were analyzed before and after stirring with steel ball bearings to rupture intact capsules.

| | CONTROL Unstirred | Stirred | CAPSULES Unstirred | Stirred |
|---|---|---|---|---|
| Headspace | 14 | 36 | 115 | 838 |
| Ratio Stirred/Unstirred | — | 3 | — | 7 |

Clearly, the presence of capsules enhanced the headspace both before and after capsule rupture. More importantly, because the fragrance was stored inside the capsule, approximately 7 times the headspace was observed after stirring than before stirring with the capsule containing experiment, while the Control with neat fragrance increased only 3 times from a much lower unstirred measurement.

The fabrics were also evaluated via bench top sensory testing. The fabric odor of those treated with capsules was clearly more noticeable and stronger than the Control, from which fragrance was not noticeable. This example demonstrates that the capsules with the NEOBEE M5 oil absorbed and held the fragrance within the capsule. This clearly demonstrates the ability to shift from fragrance leaching to fragrance absorption into the capsule with proper core design and level of use.

EXAMPLE 6

The following data illustrate how the core solvent and its level affect the performance of capsules.

Three capsules samples were made with 20%, 50% and 80%, respectively, NEOBEE M5 oil inside the capsule while the remaining portion (80%, 50% and 20%, respectively) was an IFF commercially sold fragrance fabric softener fragrance. A capsule containing 20% by weight di-isodecyl aditapate and 80 weight percent of the same fragrance in the core was also prepared.

Each of the capsule samples and a neat fragrance (control) were used as the sole fragrance source in a sample of fabric softener. A lab made fabric softener base was used which contained approximately 9% quaternary amine as the primary active. All samples had the same level of added fragrance. The four samples were tested before storage, and then aged at 37° C. for two weeks and tested again. For both tests, the samples were diluted in water and then used to rinse cloth swatches in an identical lab bench test. The fabrics were air dried and the headspace of an equal mass of fabrics were analyzed before and after stirring with steel ball bearings to rupture intact capsules. The higher the headspace, the better the performance. The performance initially, i.e. before storage is presented as an indication that initially all of the samples performed similarly.

The data below for the stored samples shows that as the level of oil is increased from 20 to 80%, the headspace values remained more constant after storage, strongly supporting the point that the solvents help stabilize the fragrance inside by reducing fragrance leaching from the capsule and allowing fragrance to be stored in the capsules.

While using a solvent called "DIDA" @ 20% (diisodecyl adipate), the headspace concentration was only 1236, much lower than the 2985 headspace concentration from NEOBEE M5 at the same 20% level. This indicates that solvent selection is also important to achieve stability.

| NEOBEE % | Stirred HeadSpace Before Storage | Stirred HeadSpace 2 wks @ 37° C. |
|---|---|---|
| Control | 471 | 361 |
| 20% | 7204 | 2985 |
| 50% | 6349 | 4946 |
| 80% | 7869 | 8611 |
| 20% NEOBEE M5 | 7204 | 2985 |
| 20% DIDA | 11829 | 1236 |

We claim:

1. A capsule particle comprising a composition containing:
    a material selected from the group consisting of a flavor material and a fragrance material, wherein at least 60 weight percent of said material have a Clog P greater than 3.3;
    a hydrophobic solvent having a Clog P greater than 3.3, wherein said hydrophobic solvent is miscible in said material; and
    a sacrificial solvent having a Clop P less than about 3, wherein said sacrificial solvent is miscible in said material and is at least about 5 weight percent of said composition;
    and an additional material encapsulating said composition.

2. The capsule particle of claim 1, wherein the sacrificial solvent is selected from the group consisting of benzyl acetate and octanol.

3. The capsule particle of claim 2, wherein the sacrificial solvent is of at least about 10 weight percent.

4. The capsule particle of claim 3, wherein the sacrificial solvent is of at least about 20 weight percent.

5. The capsule particle of claim 1, wherein the sacrificial solvent has a Clop P less than about 2.

6. The capsule particle of claim 5, wherein the sacrificial solvent has a Clop P less than about 1.5.

7. The capsule particle of claim 1, wherein the capsule particle is incorporated in a product containing a surfactant of at least about 1 weight percent.

8. The capsule particle of claim 7, wherein the product contains the surfactant of at least about 10 weight percent .

9. The capsule particle of claim 7, wherein the surfactant is selected from the group consisting of anionic, cationic and nonionic surfactants.

10. The capsule particle of claim 1 incorporated into a product selected from the group consisting of oral care products, toothpaste, lotions, creams, hair gels, antiperspirants, shaving products, colognes, bodywash, toothpaste, laundry detergents, fabric conditioners, personal care products, foodstuffs and beverages.

11. A slurry comprising:
a permeable capsule containing at least about 20 weight percent of a sacrificial solvent; and
an aqueous product base containing more than 40 weight percent of a fragrance material having a Clog P of at least about 3.3.

12. The slurry of claim 11, wherein the sacrificial solvent is selected from the group consisting of benzyl acetate and octanol.

13. The slurry of claim 12, wherein at least about 20 weight percent of the sacrificial solvent contained within the capsule migrates outside of the capsule over a period of at least one week.

14. A method of making a capsule comprising the steps of:
providing a material selected from the group consisting of a flavor material and a fragrance material and an optional hydrophobic material;
providing a sacrificial solvent having a Clog P less than about 3;
providing a permeable encapsulating material;
encapsulating said material, said optional hydrophobic material, and said sacrificial solvent with the permeable encapsulating material to provide the capsule,
whereby when the capsule is provided in a liquid environment containing an unencapsulated fragrance material, at least 20 weight percent of the sacrificial solvent migrates from the capsule into the liquid environment to come to equilibrium with the liquid environment.

15. The method of claim 14, wherein the sacrificial solvent has a Clog P of from about 1.25 to about 2.5.

16. The method of claim 15, wherein the sacrificial solvent is selected from the group consisting of benzyl acetate and octanol.

17. The method of claim 14, wherein at least about 40 weight percent of the sacrificial solvent migrates from the capsule into the liquid environment.

18. The method of claim 14, wherein the liquid environment comprises water and a surfactant.

19. The method of claim 14, wherein the unencapsulated fragrance material migrates into the capsule.

20. A capsule containing high Clog P liquid fragrance or flavor materials further comprising a sacrificial solvent having a Clog P of from about 1 to about 3, the sacrificial solvent being encapsulated with a permeable encapsulating material;
whereby the capsule is provided in a liquid environment containing unencapsulated flavor or fragrance materials with a Clog P greater than about 3.3; and whereby the sacrificial solvent leaches from the capsule into the liquid environment and the unencapsulated flavor or fragrance materials leach into the capsule.

21. The capsule of claim 20, wherein the capsule contains at least about 10 weight percent the high Clog P liquid flavor or fragrance materials.

22. The capsules of claim 20, wherein the liquid environment contains a surfactant of at least about 1 weight percent.

* * * * *